United States Patent
Miyajima

[11] Patent Number: 4,694,698
[45] Date of Patent: Sep. 22, 1987

[54] METHOD OF MEASURING FACTOR OF STRESS CONCENTRATION BY UTILIZING ULTRASOUND

[75] Inventor: Takeshi Miyajima, Makabemachi, Japan

[73] Assignee: Hitachi Construction Machinery Co., Ltd., Tokyo, Japan

[21] Appl. No.: 855,665

[22] PCT Filed: Jan. 16, 1985

[86] PCT No.: PCT/JP85/00013
§ 371 Date: Apr. 22, 1986
§ 102(e) Date: Apr. 22, 1986

[51] Int. Cl.[4] .................... G01N 29/00; G01L 1/00
[52] U.S. Cl. ............................... 73/570; 73/778
[58] Field of Search ............ 73/570, 799, 778, 862.41, 73/826, 760

[56] References Cited

U.S. PATENT DOCUMENTS 4,484,475 11/1984 Ogura et al. ..................... 73/778

Primary Examiner—Anthony V. Ciarlante
Attorney, Agent, or Firm—Wenderoth, Lind & Ponack

[57] ABSTRACT

The present invention provides a method of measuring, by utilizing ultrasound, the factor of stress concentration at a stress-concentrated portion of a member, comprising the steps of emitting ultrasound for incidence upon the stress-concentrated portion of the member in stressed state, increasing the stress in said stressed state, comparing the acoustic pressure of the reflected wave from said stress-concentrated portion between before and after the stress is changed, for thereby measuring the factor of stress concentration and by which the factor of stress concentration of a member composing a machine or the like in a static or dynamic state can be measured easily, real-time, quantitatively, nondestructively and highly accurately.

6 Claims, 33 Drawing Figures

With mean stress of $\sigma_{n1}$

With mean stress of $\sigma_{n2}$

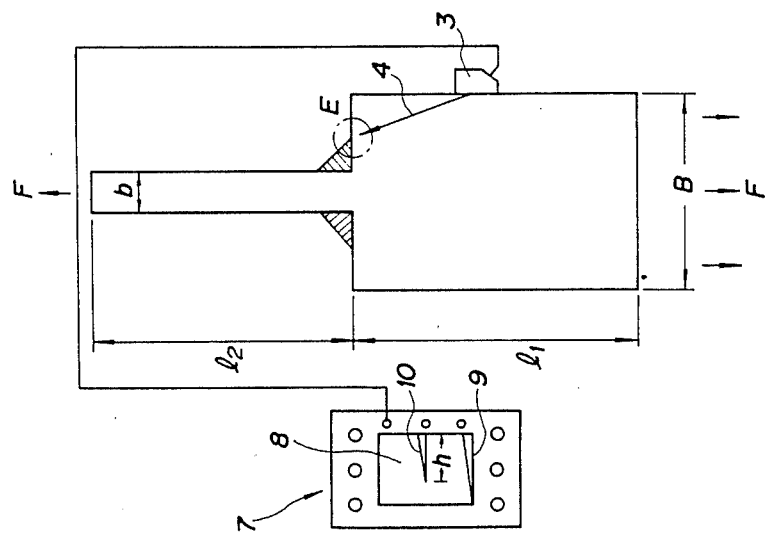
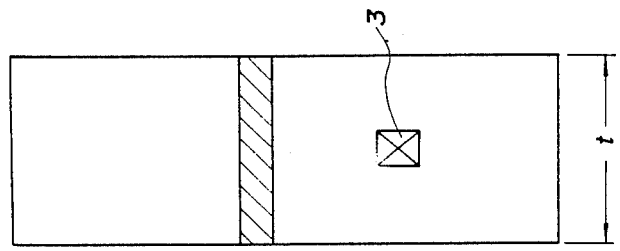
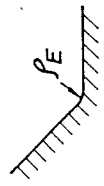
FIG. 19a
FIG. 19b
FIG. 19c

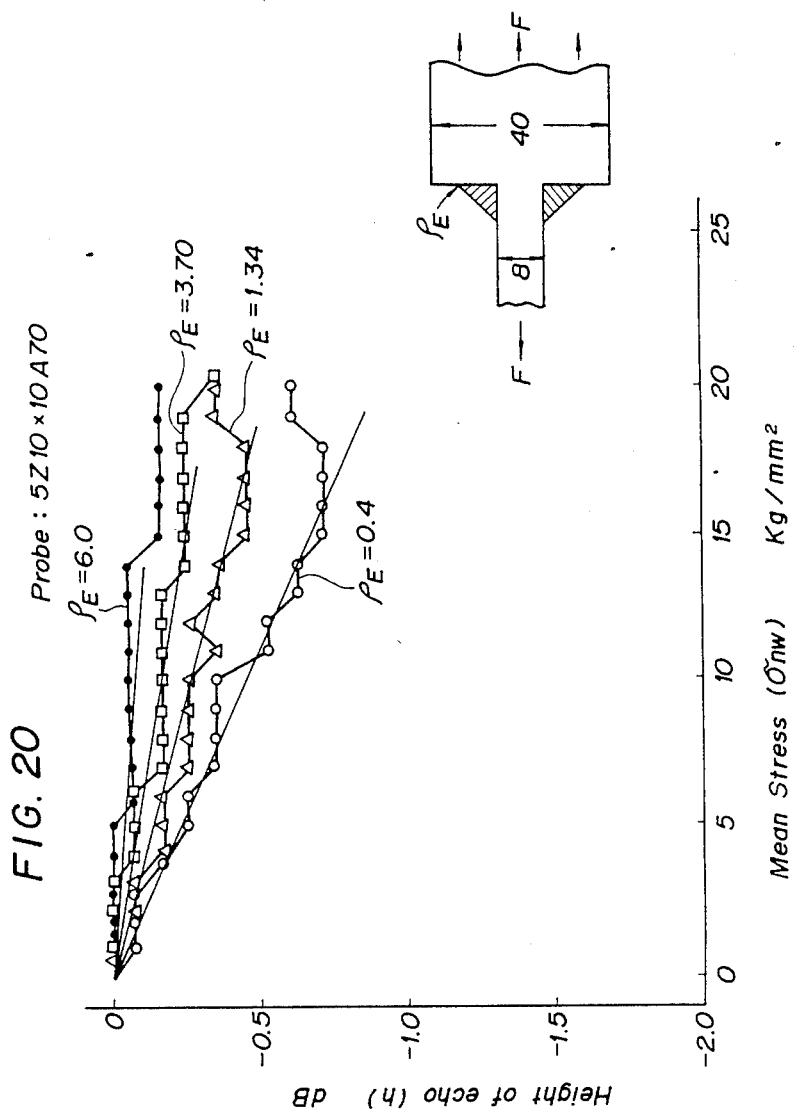

METHOD OF MEASURING FACTOR OF STRESS CONCENTRATION BY UTILIZING ULTRASOUND

BACKGROUND OF THE INVENTION (a) Field of the Invention

The present invention relates to a method of measuring, by utilizing ultrasound, the factor of stress concentration at the portion of a mechanical member, structural member or the like where stress is concentrated (will be referred to as "stress-concentrated portion" hereinafter).

The stress-concentrated portions of members, to which the present invention is applicable, include structural notched or cut portions such as hole, key way formed in members composing, for example, machineries, structures, etc. in all fields of industry, as well as undercut, blow hole, nest, crack, etc. developed in the manufacturing processes such as welding, forging, molding, etc. Also, they include the portions of materials, like flaw, crack, etc., of which the section varies abruptly.

More particularly, the present invention concerns a method of measuring the factor of stress concentration at the stress-concentrated portion of a member made of a metal or nonmetal (glass, ceramic, synthetic resin, etc.) and through which ultrasound can be propagated.

(b) Description of the prior art

Analysis concerning the stress-concentrated portion of a member, and setting of a factor of stress concentration at such portion, among others, are essential in designing and manufacturing a machine or structure in order to prevent any breakdown or damage of them and also to improve the safety and reliability. In the field of technology to which the present invention belongs, however, the method of measuring the factor of stress concentration of a real object easily, real-time and quantitatively is very important and necessary, but has not yet been established, for analysis of the stress concentration at the portions joined by the welding having been utilized from the old time and of which the application is very wide, and even for analysis of the stress concentration at the structural notched or cut portions of mechanical parts, typically, hole or key way formed by utilizing no welding and of which, it is said, the study has been highly advanced. It is very hard to theoretically analyze the mechanism of stress concentration even in these fields.

To solve the above problem, various methods of measuring the factor of stress concentration have been proposed. However, they include only the experimental methods of measuring using the photo-elasticity. That is, model experiments were made for analysis and study of only the typical models such as those in which circular holes or elliptical cavities were developed inside or on the surface of an elastic object like steel or in which U- or V-shaped notches were found on the surface of such object. These proposed methods were static, qualitative and indirect ones, and they were reported by H. Neuber and R. B. Heywood in 1958.

However, since the notches developed in the surface of bead weld vary in shape from one to another depending upon the method and kind of welding and also the shape of welded joint, the reproducibility can hardly be expected of the conventional method of measuring the factor of stress concentration at the weld zone. Therefore, it is practically impossible to condition any test piece of a weld zone into a predetermined model. In measurement of the factor of stress concentration at the welded portion, even the method of measuring by using the photo-elasticity, namely, a static, qualitative and indirect one, has some problems in applications and it is difficult to employ the method, as will be explained below.

(1) Although it is necessary to prepare a model as test piece, this modeling is impossible in practice for the above reasons.

(2) Even if such model could be prepared, since it is to be made from a material such as high-molecular epoxy resin, diarylphthalate resin or the like, differences in material, dimensions, working precision, etc. from the actual test piece are inevitably encountered which will also affect the fringe order of the stress-concentrated portion, resulting in no stable fringe order.

(3) Because of the material properties of the model, it is extremely difficult to make any acute-angle notch and so the reproduction of any stress concentration which will occur in the actual object is not expectable.

As a method of measuring the factor of stress concentration using no photo-elasticity, use of an electric resistance strain gauge (will be referred to as "strain gauge" hereinafter) is known; however, the strain gauge cannot be attached in any acute-angle notch. Even if the notch has an area wide enough to receive the strain gauge, the attaching of the strain gauge will cause of the stress-concentrated portion to have the properties changed. Thus, this method is also disadvantageous in impossibility of measuring any real factor of stress concentration. Namely, it is just an experimental method of measuring and has not been prevailing.

The present invention primarily seeks to provide a method of measuring, by utilizing ultrasound, the factor of stress concentration at the stress-concentrated portion of a mechanical or structural member, by which anyone can real-time measure the factor of stress concentration easily, quantitatively and with a high accuracy without changing the state in which the stress continuously acts on the stress-concentrated portion (will be referred to as "stressed state" hereinafter) and the nature of the portion in the stressed state.

Also the present invention seeks to provide a method of measuring the factor of stress concentration, which can measure the factor of a static stress concentration for an extremely short time (a few seconds) and also the factor of a dynamic stress concentration directly.

Furthermore, the present invention seeks to provide a method of measuring the factor of stress concentration, which can always provide for a highly accurate, quantitative measurement without being influenced by the shape and roughness of the surface on which the ultrasound probe is placed and even with more or less difference in placement of the probe.

DISCLOSURE OF THE INVENTION

The above objects are attainable by providing a method of measuring, according to the present invention, the factor of stress concentration at the stress-concentrated portion of a member in the stressed state, comprising the steps of emitting ultrasound for incidence upon said stress-concentrated portion of the member in said stressed state; increasing or decreasing the stress in said stressed state; emitting ultrasound again for incidence upon said stress-concentrated portion in the state of said increased or decreased stress; comparing the acoustic pressure of the former reflected ultrasonic wave with that of the latter one also from said stress-concentrated portion, for thereby measuring the factor of stress concentration at the stress-concentrated portion of said member taking as evaluation index the change ratio of the acoustic pressure of the reflected ultrasonic wave.

This characteristic of the present invention is to utilize the fact that when a member to be measured is continuously stressed and ultrasound is emitted for incidence upon the stress-concentrated portion of the member, there is a correlation between the change in acoustic pressure of the reflected ultrasonic wave from said stress-concentrated portion and the stress working on the stress-concentrated portion (will be referred to as "working stress" hereinafter).

FIGS. 1 to 3 explain the basic principle of the inventive method of measuring the factor of stress concentration. In these Figures, the reference numeral 1 indicates a member to be measured, 2 a stress-concentrated portion of the member 1, 3 a probe secured by an adhesive on the surface of the member 1 and which emits an ultrasound for incidence toward the stress-concentrated portion 2, 4 an incident wave of the ultrasound $P_O$ acoustic pressure of the incident wave, and 5 a reflection, or reflected wave, of the incident wave 4 from the stress-concentrated portion 2, this reflected wave being received by the probe 3.

When a tensile force $F_1$ acts on the to-be-measured member 1 within the limits of elasticity, a tensile stress develops in the member 1, a mean stress $\sigma_{n1}$ obtained by dividing the tensile force $F_1$ by a minimum sectional area, namely, an area except for the stress-concentrated portion 2, of the to-be-measured member 1 is distributed, and a maximum local stress $\sigma_{max}$ corresponding to the tensile stress $F_1$ develops in the notched bottom of the stress-concentrated portion 2. By emitting an ultrasound under an acoustic pressure $P_0$ from the probe 3 for incidence toward the stress-concentrated zone 2 in the above condition, the incident wave 4 reaches the stress-concentrated portion 2, reflected there and received as a reflected wave 5 of the acoustic pressure $P_1$ by the probe 3. Next, by increasing the tensile force $F_1$ up to $F_2$, the mean stress $\sigma_{n1}$ increases up to a mean stress $\sigma_{n2}$. The result of a microscopic observation of the change in shape of the notched bottom a of the stress-concentrated portion 2 due to the increase in means stress from $\sigma_{n1}$ to $\sigma_{n2}$ is shown in FIGS. 2 and 3. In FIG. 2, the mean stress is $\sigma_{n1}$, the notched bottom retains its initial shape and the acoustic pressures of the incident wave 4 and reflected wave 5, respectively, are $P_0$ and $P_1$, respectively. FIG. 3 shows a case in which the mean stress is increased to $\sigma_{n2}$ with the notched bottom elastoplastically changed in shape, showing the changes in shape, area, etc. which influence the acoustic pressure of the reflected wave 5. The incident wave 4 emitted under the acoustic pressure $P_0$ is so influenced by the plasto-elastical deformation of the notched bottom of the stress-concentrated portion 2 as to have the acoustic pressure decreased, and thus the incident wave becomes a reflected wave 5 of an acoustic pressure $P_2$ which is to be received by the probe 3. As the mean stress changes, the acoustic pressure changes correspondingly in this manner. However, even if the mean stress remains constant, not changed, the reflected wave has the acoustic pressure changed as the case may be. This is because the notch in the stress-concentrated portion 2 is sharp, so that the notched bottom is deformed elastoplastically in the same manner as if the working stress increases although it does not actually increase, resulting in the change of the acoustic pressure of the reflected wave as influenced by the elasto-plastical deformation. That is to say, the greater the factor of stress concentration, the larger the elastoplastical deformation of the notched bottom of the stress-concentrated portion 2 and also the change in acoustic pressure of the reflected wave. The inventive method of measuring is such that when a stress works continuously on the member to be measured, the factor of stress concentration is measured from the rate of change in acoustic pressure of the reflected ultrasonic wave caused by the elastoplastical deformation at the stress-concentrated portion.

The inventive method of measuring the factor of stress concentration will be further explained using the mathematical expressions. The ratio $P_1/P_0$ between the acoustic pressure $P_1$ of reflected wave 5 and that $P_0$ of incident wave 4 in case of the mean stress of member to be measured 1 being $\sigma_{n1}$, and the ratio $P_2/P_0$ between the acoustic pressure $P_2$ of reflected wave 5 and that $P_0$ of incident wave 4 in case of the mean stress being $\sigma_{n2}$ has the values given by the following expressions (1) and (2), respectively:

$$P_1/P_0 = C_1/f(\sigma_{n1}) \tag{1}$$

$$P_2/P_0 = C_2/f(\sigma_{n2}) \tag{2}$$

where
$f(\sigma_{n1})$, $f(\sigma_{n2})$: Functions of mean stresses $\sigma_{n1}$ and $\sigma_{n2}$, respectively; these functions have larger values along with the increase of the mean stresses $\sigma_{n1}$ and $\sigma_{n2}$.
C1, C2: Constants of proportion, each determined depending upon the dimensions, shape, etc. of the stress-concentrated portion 2

The ratio between the expressions (1) and (2), namely, the ratio between $P_1/P_2$ and $P_2/P_0$, is as follows:

$$\frac{P_1/P_0}{P_2/P_0} = \frac{P_1}{P_2} = \frac{C_1/f(\sigma_{n1})}{C_2/f(\sigma_{n2})} = C_3 \frac{f(\sigma_{n2})}{f(\sigma_{n1})} \tag{3}$$

where
C3: Constant of proportion ($=C_1/C_2$)
$P_1/P_2$: Function of mean stress (which is apparent from the expression (3))
Also, the factor of stress concentration has the value given by the expression as follows:

$$\alpha = \frac{\sigma_{max}}{\sigma_n} \tag{4}$$

where
$\sigma_{max}$: Maximum stress developed in the stress-concentrated portion 2
$\sigma_n$: Mean stress
The expression (3) can be rewritten as follows because of the expression (3):

$$\frac{P_1}{P_2} = C_3 \frac{f(\sigma_{n2})}{f(\sigma_{n1})} = C_4 \cdot f(\alpha) \tag{5}$$

where
C4: Constant of proportion
$f(\alpha)$: Function of factor of stress concentration $\alpha$ The acoustic pressure $P_1$ of reflected wave in case the mean stress is $\sigma_{n1}$ can be expressed as an acoustic pressure for a small reflector as in the following:

$$P_1 = C_5 \cdot D^2(\beta,\phi) \cdot G^2(X) \cdot a_1/S \cdot r_1 \cdot CR_1 \cdot e^{-2\alpha_0 X} \tag{6}$$

Also, the acoustic pressure $P_2$ of reflected wave in case the mean stress is $\sigma_{n2}$ is expressed as follows:

$$P_2 = C_6 \cdot D^2(\beta,\phi) \cdot G^2(X) \cdot a_2/S \cdot r_2 \cdot CR_2 \cdot e^{-2\alpha_0 X} \tag{7}$$

where
- $D(\beta,\phi)$: Directivity of ultrasound
- $\phi$: Azimuthal angle of ultrasound
- $\beta$: Directional angle of ultrasound
- $G(X)$: Range characteristic of the acoustic pressure on acoustic axis (beam axis) of ultrasound
- $a_1, a_2$: Area in reflective zone, which has an influence on the acoustic pressure of reflected wave
- $S$: Apparent area of vibrator
- $CR_1, CR_2$: Shape factors of reflective zone
- $\alpha_0$: Attenuation factor of ultrasound
- $r_1, r_2$: Reflection coefficient of ultrasound
- $X$: Path length of ultrasound beam from incidence point
- $C_5, C_6$: Constants of proportion The ratio between the expressions (6) and (7), namely, the ratio $P_1/P_2$, can be expressed as follows:

$$\frac{P_1}{P_2} = \frac{C_5 \cdot D^2(\beta,\phi) \cdot G^2(X) \cdot \frac{a_1}{S} \cdot r_1 \cdot CR_1 \cdot e^{-2\alpha_0 x}}{C_6 \cdot D^2(\beta,\phi) \cdot G^2(X) \cdot \frac{a_2}{S} \cdot r_2 \cdot CR_2 \cdot e^{-2\alpha_0 x}} = \tag{8}$$

$$\frac{C_5 \cdot a_1 \cdot r_1 \cdot CR_1}{C_6 \cdot a_2 \cdot r_2 \cdot CR_2}$$

The following expression (9) is obtainable from the expressions (5) and (8):

$$\frac{P_1}{P_2} = C_4 \cdot f(\alpha) = \frac{C_5 \cdot a_1 \cdot r_1 \cdot CR_1}{C_6 \cdot a_2 \cdot r_2 \cdot CR_2} \tag{9}$$

It is apparent from the expression (9) that the acoustic pression ratio $P_1/P_2$ when the working stress is changed is a function of the factor of stress concentration $\alpha$ and also a function of the change in acoustic-pressure reflection factor ratio due to any microscopical elastoplastic deformation in the stress-concentrated portion as the working stress changes. The expression (9) explains the basic principle of the present invention.

As having been described in the foregoing, the inventive method of measuring the factor of stress concentration is to measure a change of mean stress $\sigma_n$ and a ratio between different reflected-wave acoustic pressures $P_1$ and $P_2$ in the state with the mean-stress change, for thereby determining a factor of stress concentration from the expression (9). These values can be easily determined by means of a well-known measuring apparatus and calculator. As apparent from the expression (3), the value of incident-wave acoustic pressure $P_0$ is set off, so that the measurement is not affected by the acoustic pressure $P_0$ of the incident wave, for example, by the contact of the probe, shape and roughness of a portion to which the probe is applied. Thus, a high accuracy of measurement can be attained. Therefore, the inventive method of measuring the factor of stress concentration permits to measure the factor of a static stress concentration as well as of a dynamic stress concentration in a real object quantitatively, highly accurately and real-time.

The basic principle of the inventive method was proved by the experiments as follows:

It will be explained with reference to FIGS. 4 to 15. A portion of the test piece used in the experiments is shown in FIG. 4. The test piece has the dimensions of 35 mm (in large width B) or 20 mm (in small width b), 200 mm (in length $l_1$ and $l_2$ with the large and small widths) and 50 mm (in constant thickness t); the radii of curvature $\rho$ of the fillet weld in which stress is concentrated are in 7 kinds: 0.08, 0.21, 0.39, 0.66, 1.42, 1.90 and 2.75 mm. For facilitating to measure the radius of curvature $\rho$, a model was made of the fillet weld by means of a model duplicator, cut into slices, and each slice was put in a light projector and magnified more than 20 times for measurement. The test piece was shaped by modeling the fillet weld zone of a Tee weld joint as in FIG. 5$a$ with the radius of curvature $\rho$ as shown in FIG. 5$b$ and machining the fillet weld zone. The radii of curvature $\rho$ are in 7 kinds as as in the above. The material of the test pieces was SM50A (JIS G3106 "Rolled steel for welded structure"), and the accuracy of finishing was 240 $\mu$mRz at the portion of the radius of curvature $\rho$ and 120 $\mu$mRz at the other portions (JIS B0601 "Mean roughness at cross point in definition and display of surface roughness).

The experiments were conducted using the apparatus shown in FIG. 6. First, the probe 3 placed on the surface of the test piece 6 was secured on the test-piece surface in such a manner that the ultrasonic wave emitted from the probe 3 was incident toward the stress-concentrated portion 2. The probe 3 was connected to an ultrasonic flaw detector 7 by pulse echo technique (will be referred to as "ultrasonic flaw detector" hereinafter) widely used as nondestructive flaw detector for metals. When the test piece 6 mounted in place on the Amsler universal testing machine (not shown) was applied with a tensile load F in the direction of arrow with the load changed a reflected acoustic pressure developed in the stress-concentrated portion 2 correspondingly to each of different mean stresses $\rho_n$ working on each of the tensile loads F was displayed on a CRT display 8 of the ultrasonic flaw detector 7. The acoustic pressure was read for measurement. The above-mentioned mean stress $\rho_n$ is a value obtained by dividing the tensile load F by the area of a parallel zone with the small width b. The ultrasonic flaw detector 7 was SM-80, SM-90, etc. made by Tokyo Keiki Co., Ltd. and the probe 3 was an angle beam probe made by Japan Probe Co., Ltd. The probes 3 used in the experiments were in 5 kinds: 2Z10×10A70, 5Z10×10A70, 5Z10×10A60 5Z10×10A45 and 7Z10×10A70. Since the change in acoustic pressure of the reflected wave, having taken place in the stress-concentrated portion 2 in response to the change of mean stress $\sigma_n$ was very small, the acoustic pressure of reflected wave was measured by the following method for facilitating the read and measurement:

(1) With the rejection control turned off, the echo at a lower level than a predetermined level on the CRT display 8 is not inhibited.

(2) A section paper was attached on the scale panel on the CRT display 8 and the portion equal to 10% of the scale panel was regularly divided by 20; namely, one division was made 0.5% of the scale panel.

(3) The reflected-wave acoustic pressure from the stress-concentrated portion 2 where the mean stress was $\sigma_n$ was zero set at the center (equal to 50%) of the scale panel on the CRT display 8.

(4) As the test piece 6 was applied with various tensile loads F, the reflected-wave acoustic pressure from the stress-concentrated portion 2 was read by the unit of 0.5%/ division at each of the tensile load F.

(5) The value of the acoustic pressure read by the unit of 0.5%/division at the step (4) above was displayed as echo height having been converted into decibel value, not acoustic pressure.

The reflected wave derived from the incident wave 4 emitted for incidence upon the stress-concentrated portion 2 is displayed on the CRT display 8 taking as horizontal axis the distance x from the incidence point of the incident wave 4 to the stress-concentrated portion 2 as shown in FIG. 6 and as the vertical axis the height h of the echo 10 displayed in dB. The reference numeral 9 indicates an echo of the transmitted ultrasonic wave. This is illustrated in FIG. 7.

The experiments were also conducted on the test pieces with the radii of curvature $\rho$ of the fillet weld zone being in 7 kinds as having been described. Furthermore, the experiments were done with the different radii of curvature $\rho$ and small width b in combination with said 5 types of probes. As the results, the basic principle of the inventive method of measuring the factor of stress concentration was proved as follows:

(1) The result of the experiment conducted on the relation between the change of means stress $\sigma_n$ and echo height h is shown in FIG. 8. The test piece used in this experiment has the same shape as in FIG. 4 and the dimensions: B=25. b=20, $l_1=l_2=200$ and t=50 (all in mm) which were constant. The radii of curvature $\rho$ of the fillet weld zone were in 7 kinds: 0.08, 0.21, 0.39, 0.66, 1.41, 1.90 and 2.75 (all in mm). The probe used was 5Z10×10A70 of which the frequency was 5 MHz. The experiment was conducted in the manner as having been described with reference to FIG. 6 in the foregoing. As seen from FIG. 8, when the mean stress $\sigma_n$ is on the order of 10 to 15 kg/cm², all the echo heights h displayed in db decrease almost linearly whether the radius of curvature $\rho$ is large or small, so that the linear expression (10) is established:

$$h = -a\sigma_n \tag{10}$$

where
a: Constant of proportion indicative of gradient

Next, while the means stess $\sigma_n$ is being 10 to 20 kg/mm², the echo height h is nearly constant although the radius of curvature $\rho$ varies a little from one to another. When the mean stress $\sigma_n$ exceeds the above-mentioned range, the echo height h increases linearly with the test pieces of relatively large radii of curvature $\rho$ among the 7 kinds of test pieces, and the following expression (11) is established:

$$h = b\sigma_n + C \tag{11}$$

where
b: Constant of proportion
C: Constant

Within the stress region where the relation (11) is established, the stress-concentrated portion is within the limits of elasticity, and the maximum stress $\sigma_{max}$ does not exceed the yield point $\sigma_y$ of the test-piece material; therefore, it can be said that the ratio $\sigma_{max}/\sigma_n$ between the mean stress $\sigma_n$ and maximum stress $\sigma_{max}$ is precisely equal to the factor of stress concentration $\alpha$. Meanwhile, in the stress region where the echo height h is nearly constant, the maximum stress $\sigma_{max}$ in the stress-concentrated portion exceeds the yield point $\sigma_y$ of the test piece material and the strain increases in the condition without any change in stress of the stress-concentrated portion, which is caused by the so-called "sliding deformation". In the stress region in which the echo height h increases, the test piece incurs a further increased plastical deformation, which, it is estimated, is caused by the change in shape of the stress-concentrated portion in any manner other than the elastic deformation.

Also as apparent from FIG. 8, when the mean stress $\sigma_n$ is a maximum of about 10 kg/mm², the echo height h has a larger gradient as the radius of curvature $\sigma$ is smaller. On the other hand, it was reported on the page 632 of the paper entitled "Stress Concentration" (published bby Morikita Shuppan in 1973) that the solid solution of factor of stress concentration was obtained in the following form as the results of experiments on the photo-elasticity:

$$\alpha = 1 + \left[ \frac{\frac{B}{b} - 1}{\left(2.8 \cdot \frac{B}{b} - 2\right)} \cdot \frac{b}{\rho} \right]^{0.65} \tag{12}$$

By calculating the factor of stress concentration $\alpha$ from the expression (12) and determining the constant of proportion a in the above-mentioned expression (10), by the method of least squares, as to each radius of curvature $\rho$ in the experiment results shown in FIG. 8, the relation between the factor of stress concentration and the constant of proportion is plotted as indicated with small circles in FIG. 9. As seen from FIG. 9, there is a linear relation between the logarithmic value of the factor of stress concentration $\alpha$ and the constant of proportion a indicative of the gradient $h/\sigma_n$. The regression expression of the constant of proportion a determined, by the method of least squares, in relation with the factor of stress concentration $\alpha$ will be as follows:

$$a = -0.158 \log \alpha \tag{13}$$

It is seen that the above expression depicted with a straight line generally coincides with the plotting with small circles as shown in FIG. 9. The error of the straight linn from each plotted point is as small as less than 20% in case the factor of stress concentration $\alpha$ is less than 5. As seen evident from the relation between the mean stress $\sigma_n$ and echo height h, the factor of stress concentration $\alpha$ could be determined with an accuracy sufficiently high in practice and quantitatively. The relation between the mean stress $\sigma_n$ and echo height h is expressed as follows based on the expressions (10) and (13)

$$h = (-0.158 \log \alpha)\sigma_n \tag{14}$$

(2) It is considered from the expression (12) that the factor of stress concentration $\alpha$ of the test piece used in the above-mentioned experiment was influenced by the radius of curvature $\rho$ as well as the test piece widths B and b. Experiment was effected in the procedure shown in FIG. 6 as in FIG. 8 (the probe of 5 MHz was used) on the test pieces of the same shape as in FIG. 4 and radii of curvature $\rho$: 0.74. 0/76, 1.65 and 3.50 mm but with the small width b of 29 mm instead of 20 mm. The results of this experiment are shown in FIG. 10. As shown in FIG. 10, the relation between the mean stress $\sigma_n$ and echo height h is similar in numerical value and gradient to the results shown in FIG. 8. The relation between the constant of proportion a indicative of the gradient in the region where the expression (10) is established (mean stress $\sigma_n$ being on the order of 10 to 15 kg/cm$^2$) and the factor of stress concentration $\alpha$ can be determined from the expression (12), and is indicated with small circles in FIG. 11. The regression expression of the constant of proportion a in relation with the factor of stress concentration $\alpha$ was determined to be identical to the expression (13), and it is shown with a straight line in FIG. 11.

(3) The results of an experiment conducted on the influence of the refraction angle of the probe on the relation between the mean stress $\sigma_n$ and echo height h is shown in FIG. 12. The parameter is the refraction angle of the probe. The test piece used in the experiment has the same shape as in FIG. 4 and is the same in other respects as in FIG. 4 except for the radius of curvature $\rho$ being 0.66 mm. Also, the probes used are of 4 MHz in frequency as in the above experiment and of three kinds of refraction angle: 45°, 60° and 70°. The factor of stress concentration $\alpha$ of this test piece is 3.43 as calculated based on the expression (12). As known from the results of this experiment, the relation between the mean stress $\sigma_n$ and echo height h is so little influenced by any difference in refraction angle among the probes that it may be depicted with a straight line. However, use of a probe larger in refraction angle, which permits to effect an ultrasonic measurement from a place distant from the stress-concentrated portion so that the deformation of the probe-attached portion due to the stress in the stress-concentrated portion is minimized, improves the accuracy of measurement.

(4) FIGS. 13 and 14 show the results of the experiments conducted on how the change of the probe frequency f influenced on the relation between the mean stress $\sigma_n$ and echo height h. The test piece used in the experiment has the same shape as in FIG. 4 and it is the same in other respects as in the above-mentioned experiment except for the radii of curvature $\rho$ of the fillet weld being 0.08, 0.21, 0.39, 0.66 and 2.75 mm (5 kinds). The probes used in this experiment include a one of 2 MHz in frequency (2Z10×10A70) with the results in FIG. 13 and another of 7 MHz in frequency (7Z10×10A70) with the results in FIG. 14. So, the experiments were done in the same manner as having been described with reference to FIG. 6 as in FIG. 8 (the probe of 5 MHz was ued). Both the experiment results in FIGS. 13 and 14 have a same tendency as that in FIG. 8 which has been described in (1) above. From these experiment results, the following was proved. Namely, (i) The higher the probe frequency f, the greater the gradient of the echo height h, namely, the value of the constant of proportion a in the expression (10), so that the accuracy of measurement is so higher. (ii) The lower the frequency f, the smaller the variation of the echo height h with respect to the mean stress $\sigma_n$ and the higher the linearity of the gradient. As apparent from these experiment results, a probe frequency on the order of 5 MHz meet the requirements for both the accuracy of measurement and the linearity of gradient. As having been described in the above, the refraction angle of the probe should preferably be large. Thus, the probe which will be referred to in the following explanation is 5Z10×10A70 of 70° in refraction angle unless otherwise noted.

Experimental expressions on the relation between the mean stress $\sigma_n$ and echo height h determined with probe frequencies f of 2 MHz and 7 MHz by the method described in (1) will be as follows:

With 2 MHz:

$$h = (-0.07 \log \alpha)\sigma_n \quad (15)$$

With 7 MHz:

$$h = (-0.185 \log \alpha)\sigma_n \quad (16)$$

The relations between the gradients in the experimeneral expressions (14), (15) and (16) and each of the frequencies f are shown with small circles in FIG. 15. The horizontal axis of the graph in FIG. 15 is the logarithmic value of frequency f (MHz) while the vertical axis is the gradient A of the experimental expression. As seen from FIG. 15, there is a linear relation between the gradient A and the logarithmic value of frequency f. The regression expression of this relation is as follows:

$$A = -0.213 \log f - 0.007 \quad (17)$$

where f: Probe frequency (MHz)

The relation between the mean stress $\sigma_n$ and echo height h, including the probe frequency f, can be derived as follows from the expression (17):

$$h = [(-0.213 \log f - 0.007) \log \alpha]\sigma_n \quad (18)$$

The echo height h can be expressed in the form of a simple expression which can be determined from a probe frequency f, factor of stress concentration $\alpha$ and mean stress $\sigma_n$. The factor of stress concentration $\alpha$ can be expressed as follows based on the expression (18):

$$\alpha = \frac{h}{10^{(-0.213 \log f - 0.007)\sigma_n}} \quad (19)$$

The relation (19) can be used to determine a factor of stress concentration $\alpha$ from the values of an echo height h, probe frequency f and mean stress $\sigma_n$. Among these factors, the frequency f is a known value depending upon a probe to be used, and the value of the mean stress $\sigma_n$ can be easily determined from a known sectional area of a member under measurement if the value of a load working on the member having a stress-concentrated portion is known. In effect, by determining the value of the third factor, namely, the echo height h, on the CRT display of the measuring apparatus, the factor of stress concentration $\alpha$ can be determined from the expression (19).

Therefore, with the present invention, it is possible to determine the factor of stress concentration in the stress-concentrated portion of a to-be-measured member on the basis of the expression (19) easily, quantitatively, highly accurately and nondestructively. Also, the factor of stress concentration can be measured realtime by measuring the height of an echo from the stress-concentrated portion of the member of an actual product. As having been described in the foregoing, the factor of stress concentration can be determined directly, in a short time and with an accuracy equal to or higher than the value determined in the photo-elasticity experiments, by measuring the height of an echo from the stress-concentrated portion of a member under measurement. At the same time, the factor of stress concentration can be easily determined statically as well as dynamically by changing the working stress.

These and other objects and advantages of the present invention will be better understood from the ensuing description made, by way of example, of the preferred embodiments of the present invention with reference to the drawings.

BRIEF DESCRIPTION OF THE DRAWINGS

FIGS. 19a to 21 show a second example in which the present invention was applied to the measurement of the factor of stress concentration at the flange side of fillet weld zone of a Tee joint, FIG. 19a explaining the test piece and measuring apparatus, FIG. 19b being a side elevation of the test piece in FIG. 19a, FIG. 19c showing as enlarged in scale the toe of weld E of the portion to be measured, FIG. 20 showing the result of the measurement of the relation between the mean stress and echo height taking as parameter the radius of curvature of the toe of weld E, and FIG. 21 being a graph indicative of the relation between the radius of curvature and factor of stress concentration, determined from the measurement result in FIG. 20, in which regression line of the above relation is indicated with a dot line;

DETAILED DESCRIPTION OF THE PREFERRED EMBODIMENTS

The present invention will be further explained with reference to the drawings, taking as model the fillet weld zone of a Tee joint.

Figure 1:
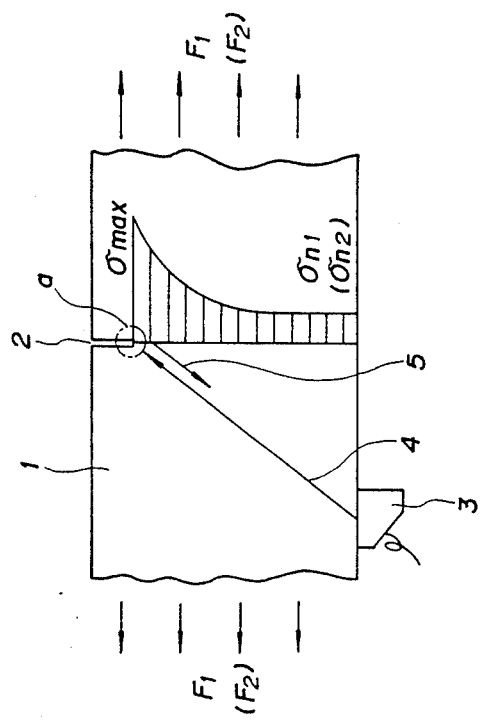
FIG. 1 explains the basic principle of the inventive method of measuring the factor of stress concentration.
Figure 2:
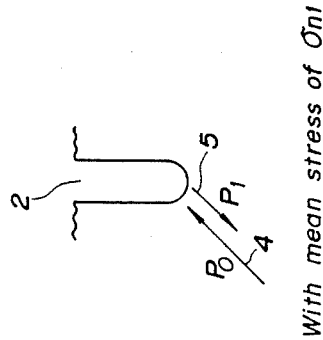
FIG. 2 is a detail view of the portion a of the stress-concentrated portion in FIG. 1, showing the stressed state of $\sigma_{n1}$ in mean stress.
Figure 3:
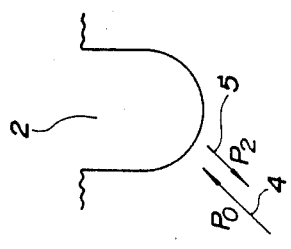
FIG. 3 explains the change from the stressed state in FIG. 2 to a stressed state of $\sigma_{n2}$ in mean stress.
Figure 4A:
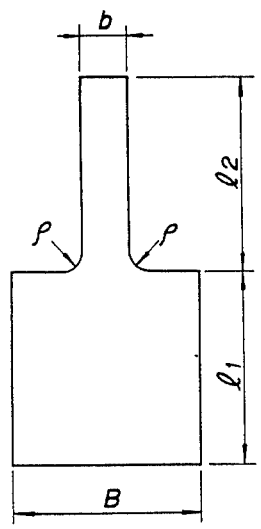
FIG. 4 explains the shape of the test piece used in the experiment effected to prove the basic principle of the inventive method of measuring the factor of stress concentration.
Figure 4B:
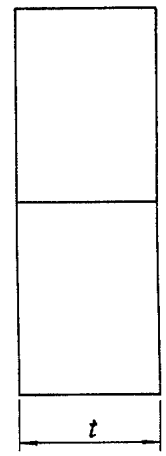
Figure 5A:
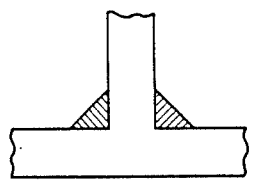
FIG. 5a shows the fillet weld zone of a Tee joint.
Figure 5B:
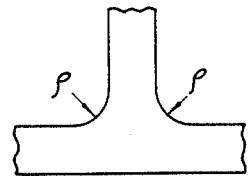
FIG. 5b shows the modeling of the fillet welded portion in FIG. 5a by finishing the fillet weld zone so as to have a radius of curvature $\rho$.
Figure 6:
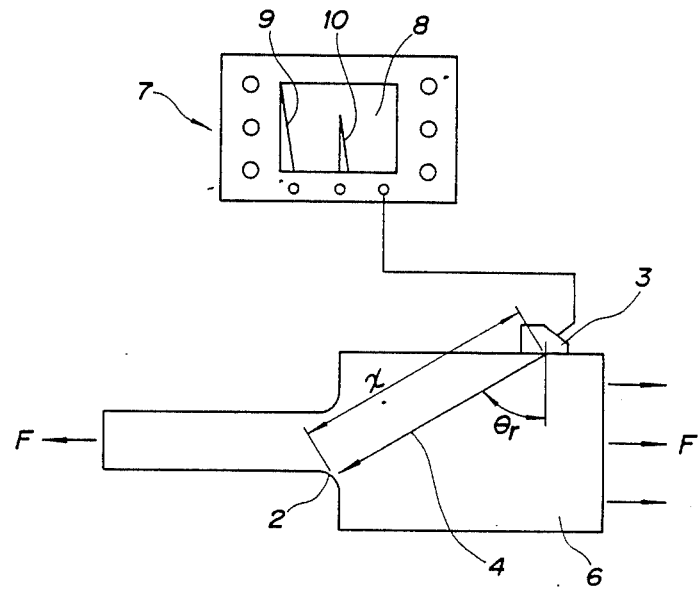
FIG. 6 explains the experimental device using the test piece in FIG. 4.
Figure 7:
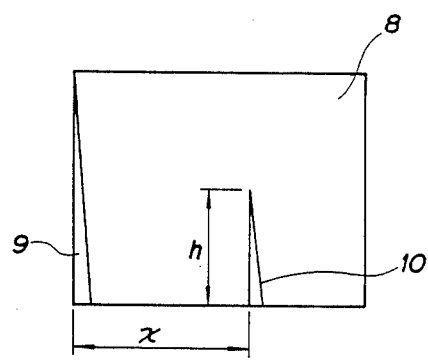
FIG. 7 explains as enlarged in scale the display on the CRT screen of the experimental device in FIG. 6.
Figure 8:
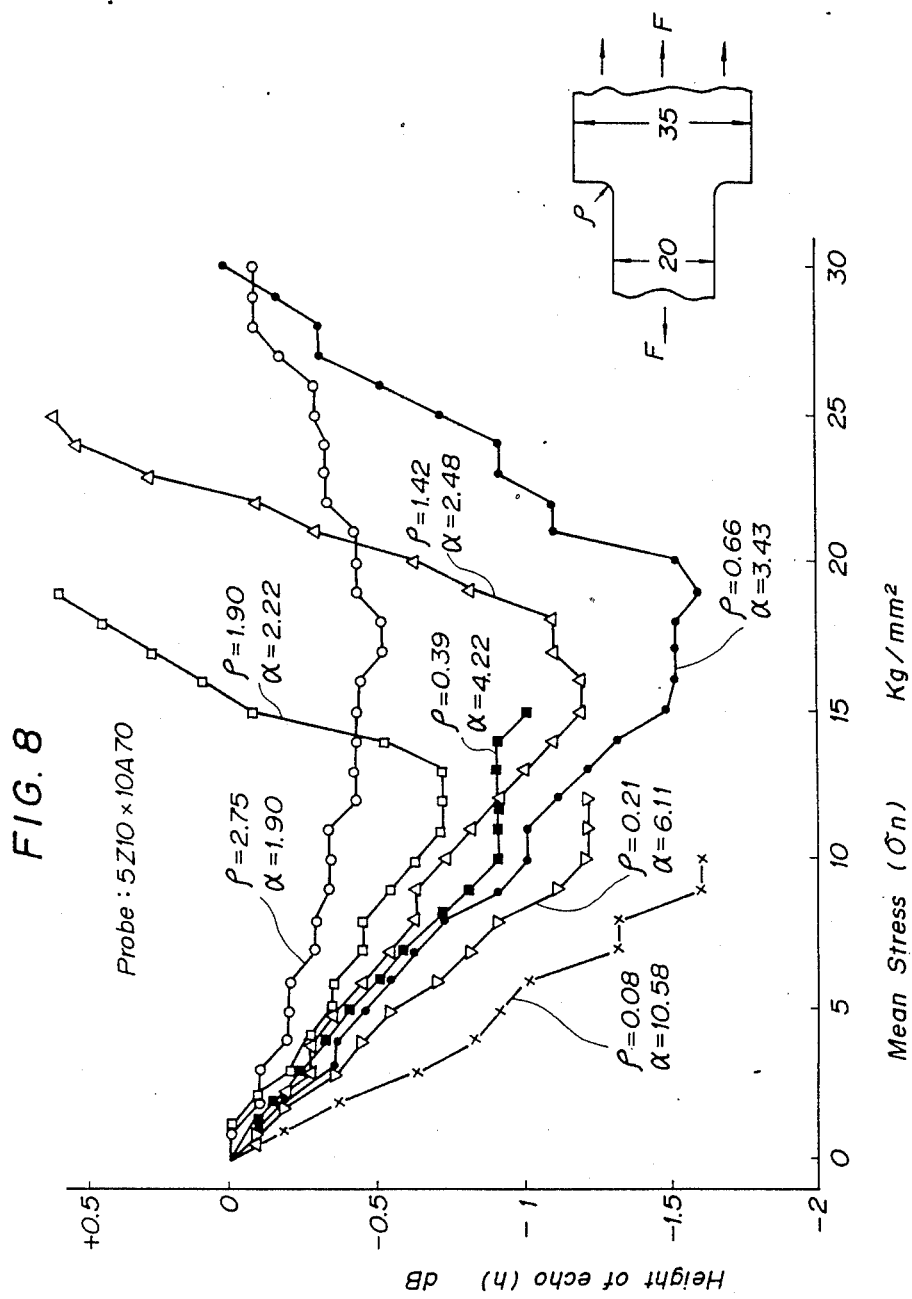
FIG. 8 shows one example of the result of an experiment in which the relation between the mean stress and echo height was determined taking as parameter the radius of curvature of the stress-concentrated portion.
Figure 9:
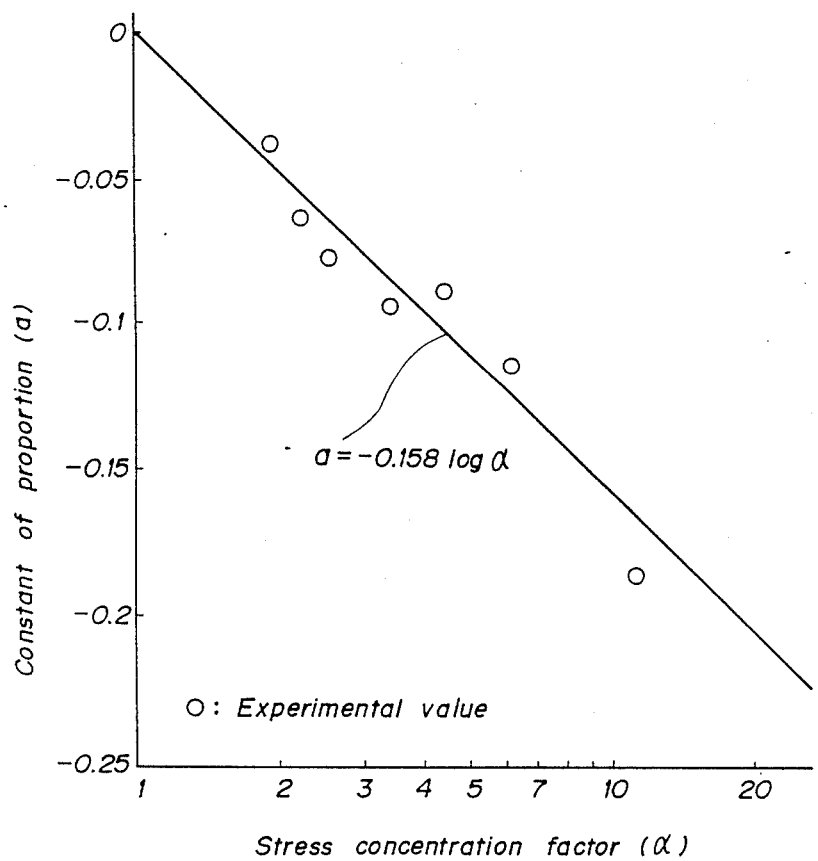
FIG. 9 shows the correlation between the factor of stress concentration in FIG. 8 and the constant of proportion indicative of the gradient of the relation between the mean stress and echo height.
Figure 10:
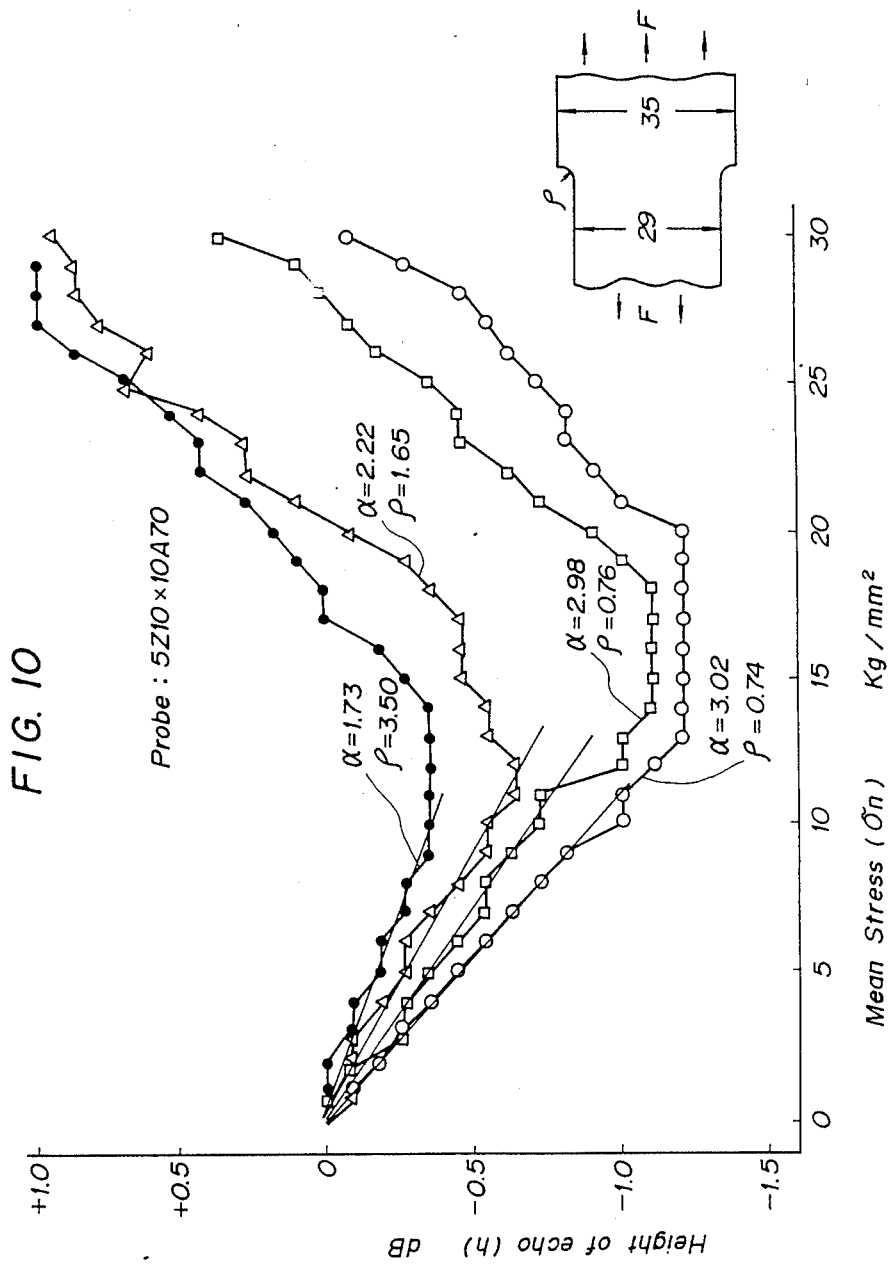
FIG. 10 shows one example of the result of an experiment in which the relation between the mean stress and echo height was determined with the test piece width and radius of curvature of the stress-concentrated portion changed.
Figure 11:
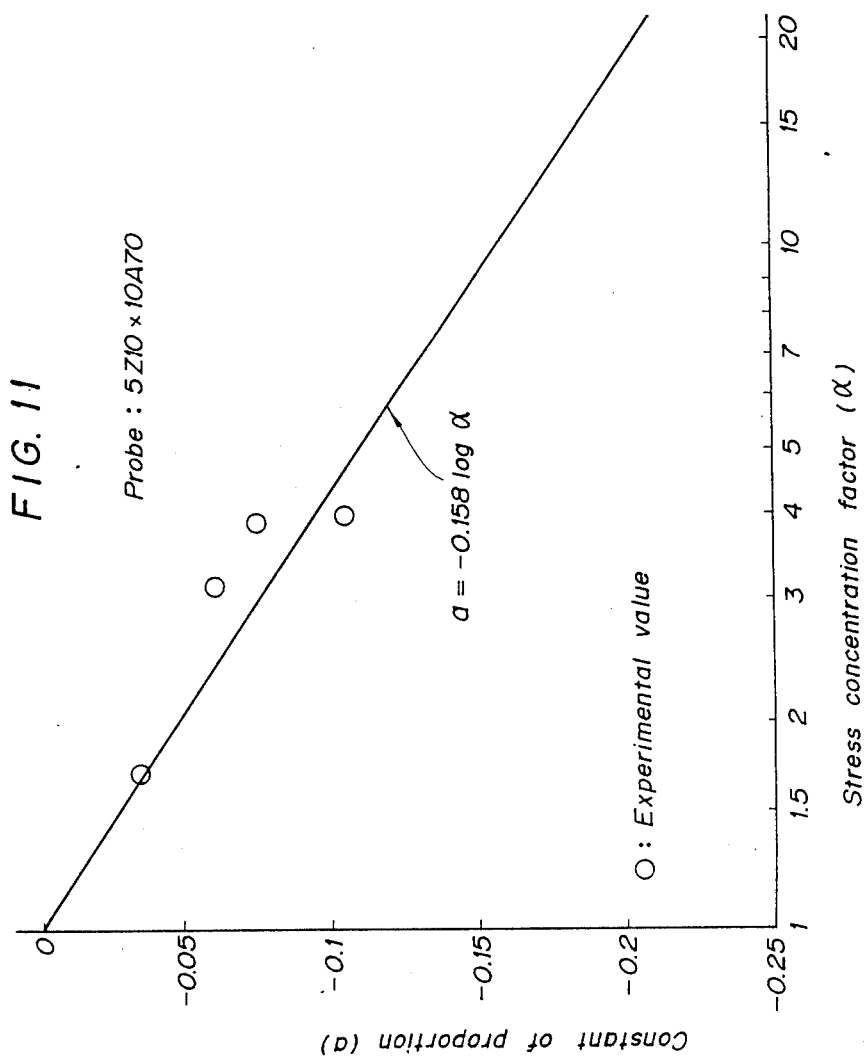
FIG. 11 shows the correlation between the factor of stress concentration in FIG. 10 and the constant of proportion indicative of the gradient of the relation between the mean stress and echo height.
Figure 12:
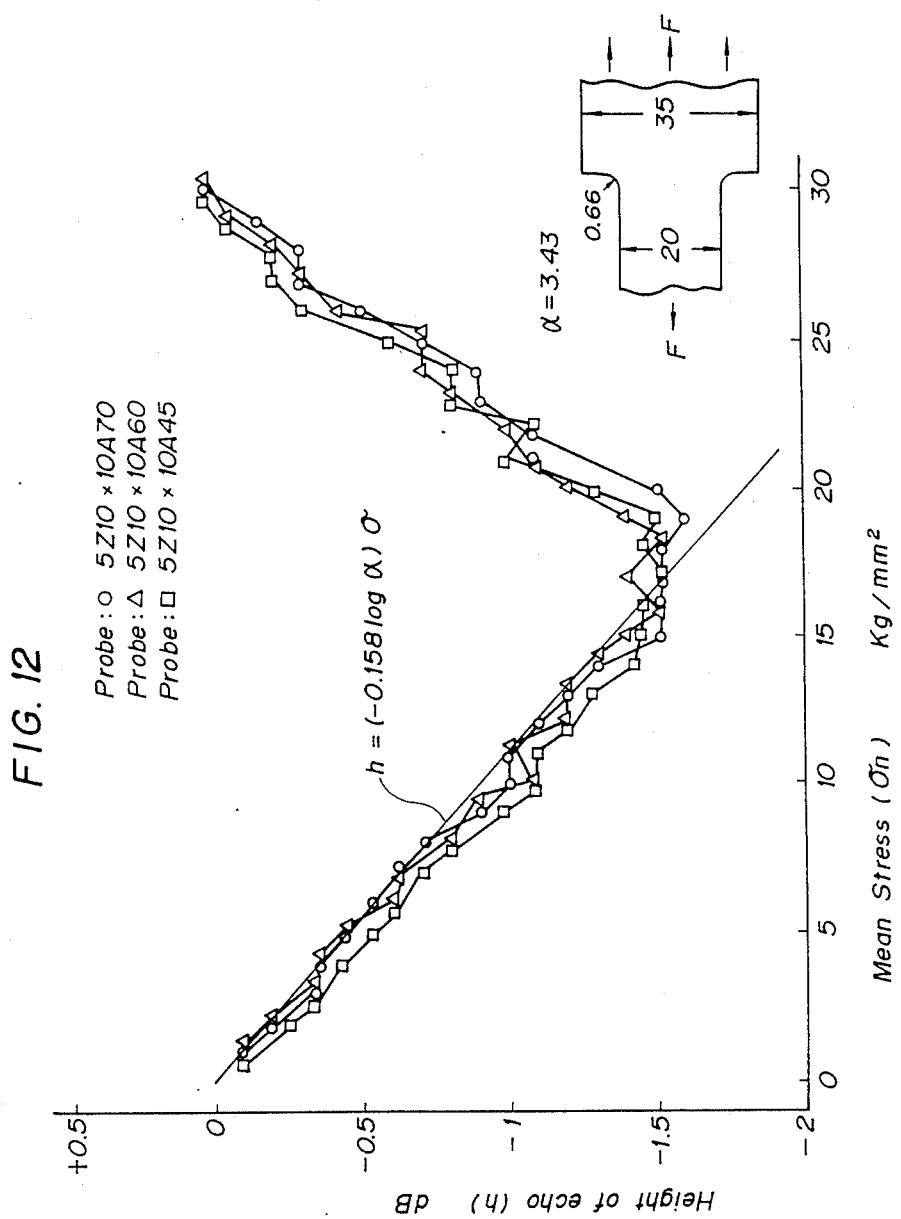
FIG. 12 shows one example of the result of an experiment in which the relation between the mean stress and echo height was determined taking as parameter the angle of refraction of the ultrasound probe.
Figure 13:
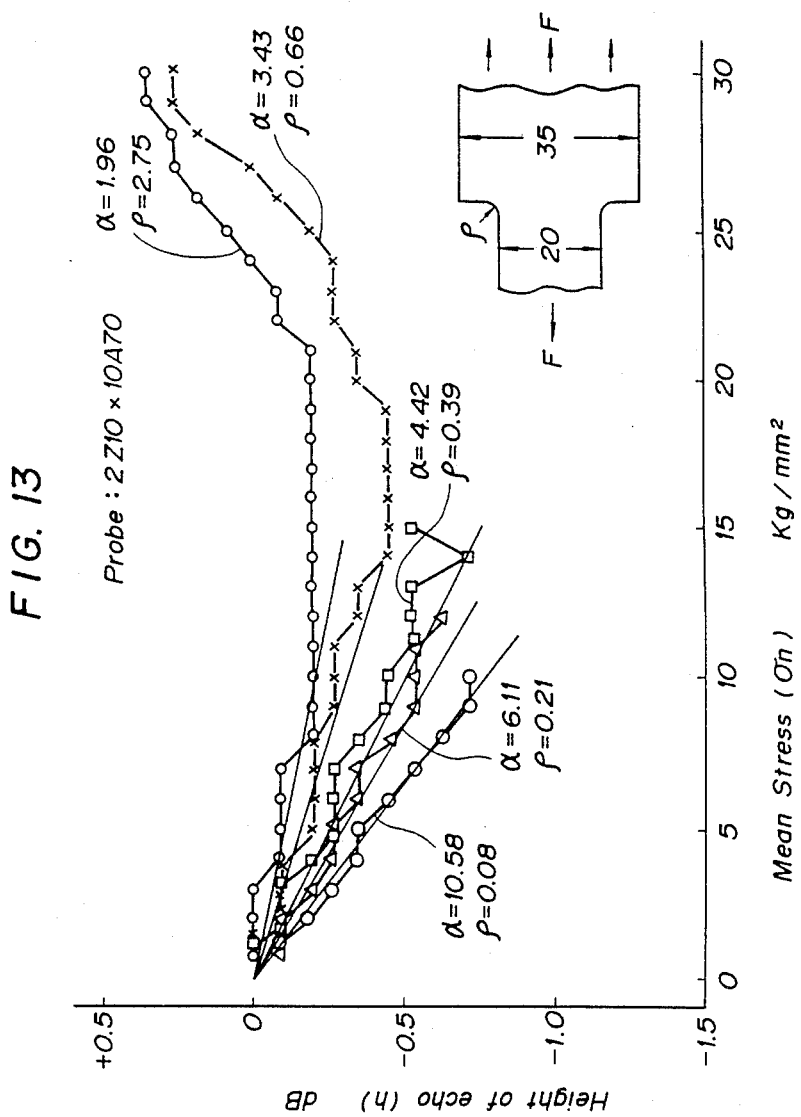
FIG. 13 shows one example of the result of the experiment in FIG. 8 having been done with the probe frequency changed.
Figure 14:
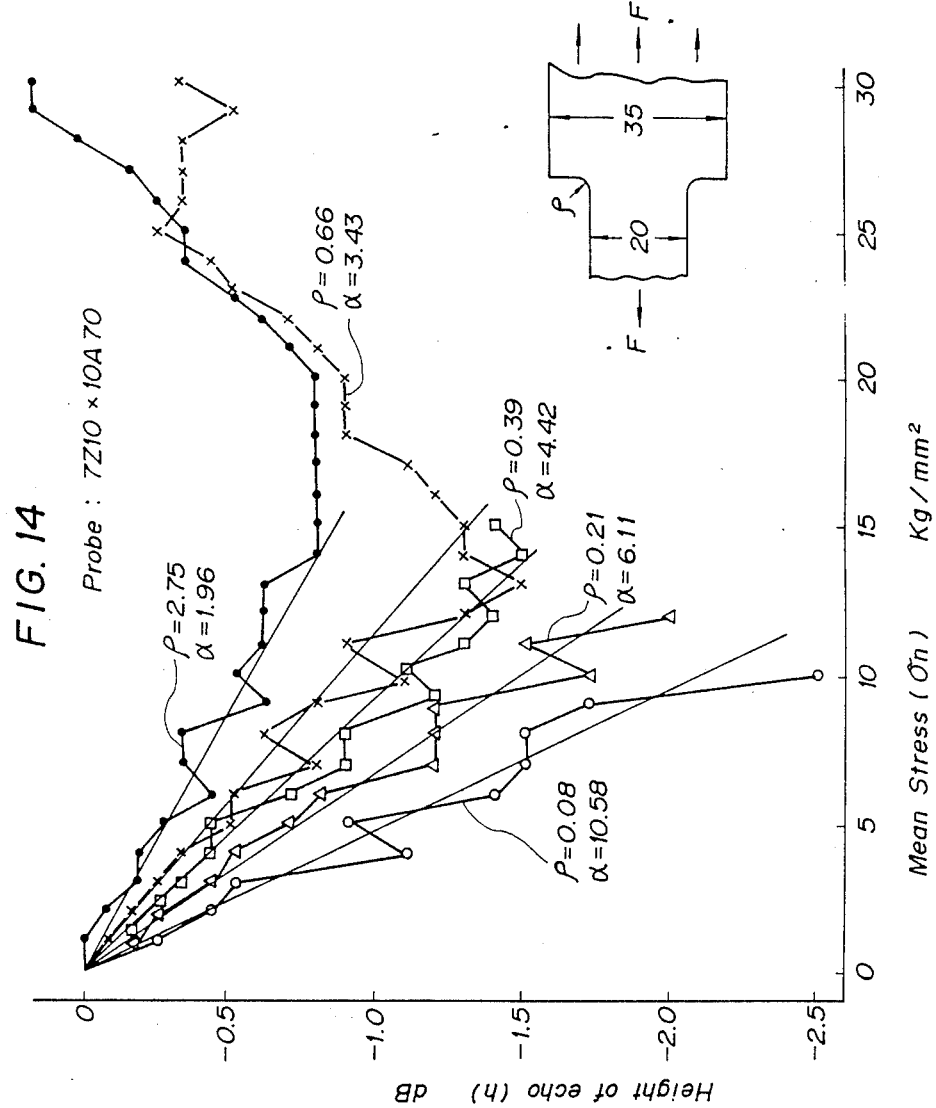
FIG. 14 shows the result of the experiment in FIG. 13 having been done with the probe frequency changed.
Figure 15:
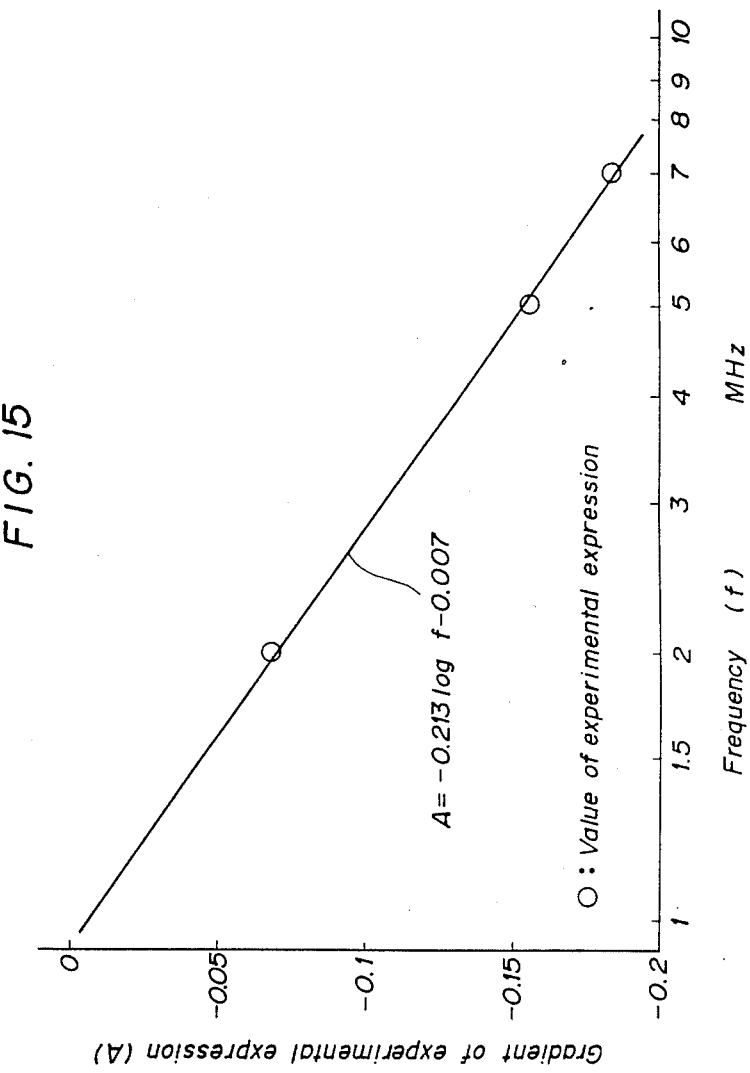
FIG. 15 shows the correlation between the gradient of the experimental expression by which the relation between the mean stress and echo height was determined with the probe frequency changed, and that probe frequency.
Figure 16A:
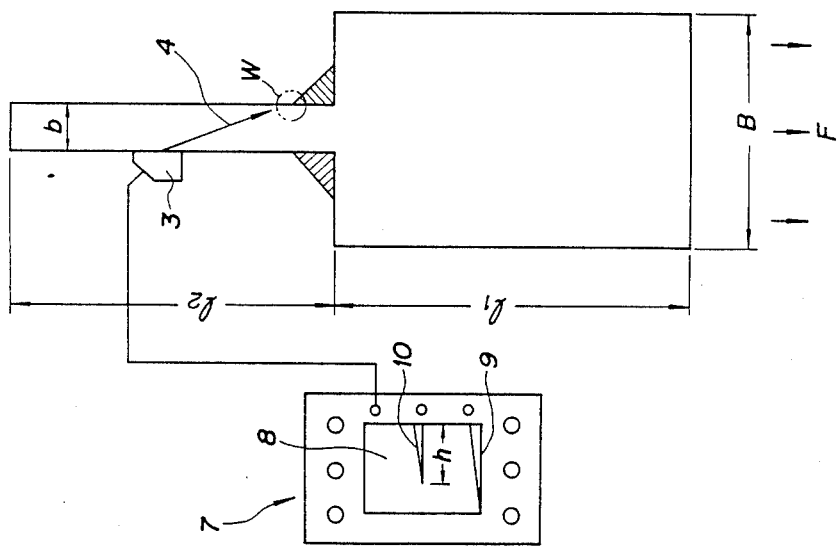
FIGS. 16a to 18 show a first example in which the present invention was applied to the measurement of the factor of stress concentration at the web side of fillet weld zone of a Tee joint, FIG. 16a explaining the test piece and measuring apparatus, FIG. 16b being a side elevation of the test piece in FIG. 16a, FIG. 16c showing as enlarged in scale the toe of weld W of the portion to be measured, FIG. 17 showing the result of the measurement of the relation between the mean stress and echo height taking as parameter the radius of curvature of the toe of weld W, and FIG. 18 being a graph indicative of the relation between the radius of curvature and factor of stress concentration, determined from the measurement result in FIG. 17, in which the regression line of the above relation is indicated with a dot line.
Figure 16B:
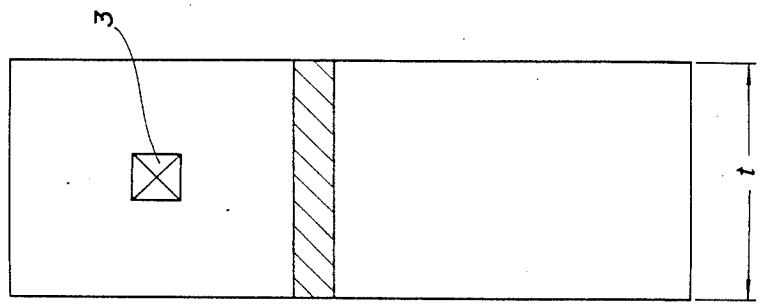
Figure 16C:
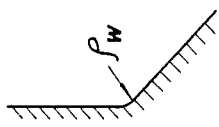
Figure 17:
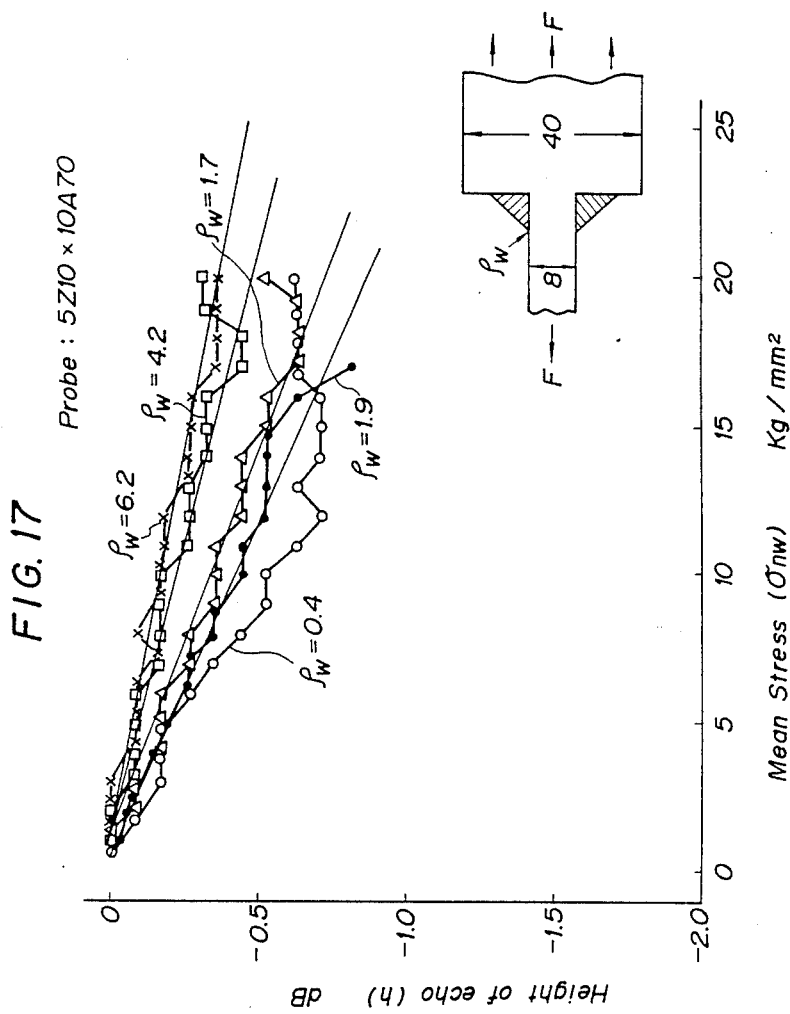
Figure 18:
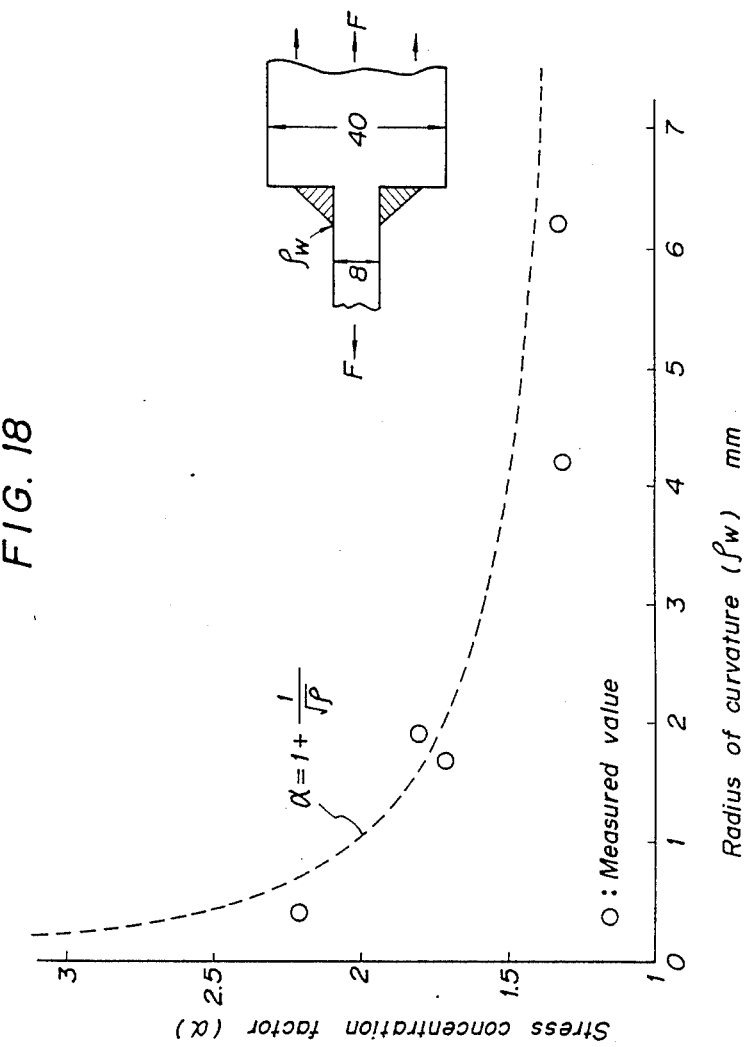
Figure 21:
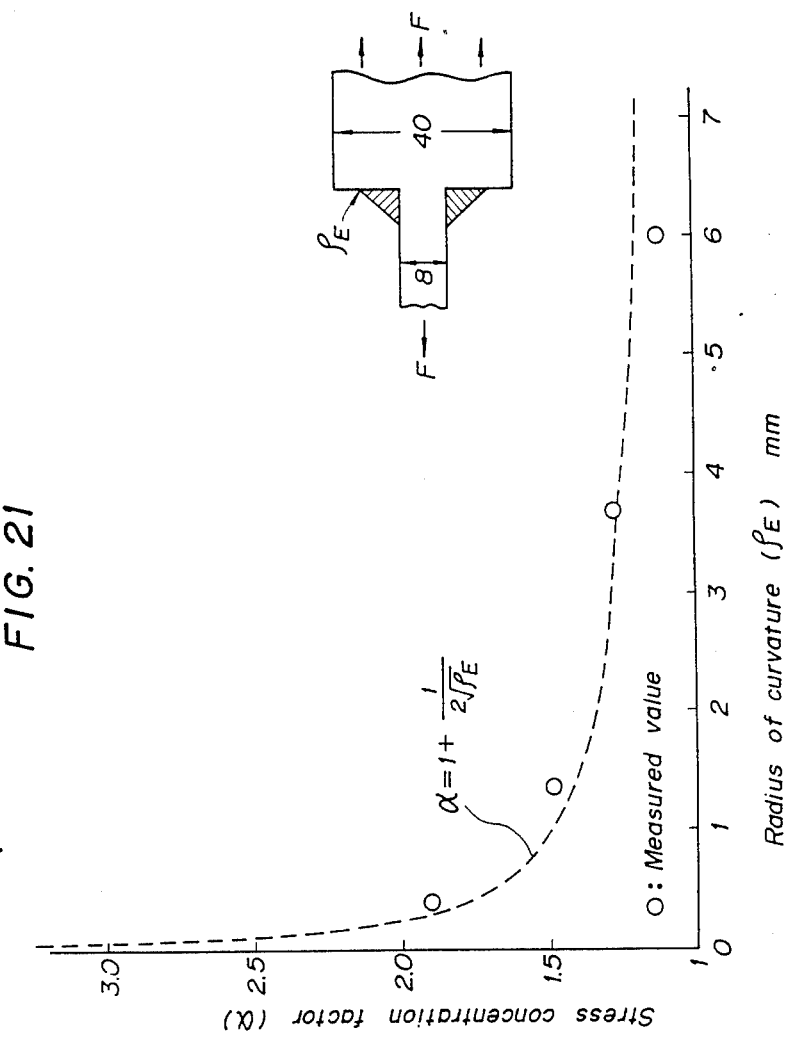

FIGS. 16 to 18 explain a first embodiment of the present invention, among which FIGS. 16a and 16b provide explanation of the test piece and an apparatus to measure the factor of stress concentration in the weld zone of the test piece. The test piece has the flange width B of 40 mm at the T joint and web width b of 8 mm, the flange thickness $l_1$ and web height $l_2$ both of 200 mm, and the length t of 50 mm. The weld zone is a weld bead of 8 mm leg length, which is formed by a semi-automatic $CO_2$ arc welding. FIG. 16c shows as enlarged in scale a toe of weld W at the web side which is the stress-concentrated portion in FIG. 16a. The toe of weld W has 5 kinds of radius of curvature $\rho_w$: 0.4, 1.7, 1.9, 4.2 and 6.2 mm. The radii of curvature $\rho_w$ were measured in the same manner as having been described concerning the test piece shown in FIG. 4. The material of the test piece is SM50A, the same as that of the test piece shown in FIG. 4. The toes of weld other than that W of the member under measurement were finished by a grinder so as to have a sufficiently large radius of curvature to prevent the toe of weld W from being influenced by any stress concentration. The measuring apparatus for factor of stress concentration is similar to that shown in FIG. 6. The probe 3 placed on the web is secured by any adhesive for the ultrasound to be omitted for incidence toward the toe of weld W at the web where stress is concentrated, and then electrically connected to the ultrasound flaw detector 7. The test piece is mouned in place on the Amsler universal testering machine (not shown) and applied with a tensile load F in the direction of arrow with the load being changed in value. The types of the ultrasound flaw detectors 7 are SM-80 and SM-90 by Tokyo Keiki Co., Ltd. The type of the probe 3 is 5Z10×10A70 of which the frequency is 5 MHz and refraction angle is 70°.

When the test piece is applied with a variety of tensile loads F, a mean stress $\sigma_{nw}$ develops against each of the tensile loads F in the web. In the stressed state in which mean stresses $\sigma_{nw}$ of different values develop, the reflected wave derived from the incident wave 4 emitted from the probe for incidence toward the toe of weld W at the web side has the beam path length displayed along the horizontal axis of CRT 8, while height h of the echo 10 indicative in dB of the acoustic pressure of the reflected wave from the toe of weld B is displayed along the vertical axis.

The measurement results of the relation of the echo height h with the change of the mean stress $\sigma_{nw}$ are shown in FIG. 17. The parameter is the radius of curvature $\rho_w$ of the toe of weld W at the web side. As seen from FIG. 17, the smaller the radius of curvature $\rho_w$, the greater the change of echo height h with the change of mean stress $\sigma_{nw}$ and so the gradient of the echo height in the range of about 10 to 15 kg/mm² in mean stress $\sigma_{nw}$ in which the relation between both these factors is nearly linear, is great as compared with that with a larger radius of curvature $\rho_w$. By substituting this relation in the expression (19), a factor of stress concentration $\alpha$ of the toe of weld W can be easily determined for each mean stress $\sigma_{nw}$. The relation between the radius of curvature $\rho_w$ and the factor of stress concentration $\alpha$ obtained from the expression (19) is shown with small circles in FIG. 18. The regression line, formed by connecting the small circles, which indicates the relation between the factor of stress concentration $\alpha$ and radius of curvature $\rho_w$, is expressed as follows:

$$\alpha = 1 + \frac{1}{\sqrt{\rho_w}} \quad (20)$$

As seen from this relation, the factor of stress concentration $\alpha$ can have an approximate value determined from only the relation with the radius of curvature $\rho_w$. As also proved with this first embodiment, the plotting with dots of the factor of stress concentration $\alpha$ determined by the expression (20) coincides relatively well with that with small circles of the factor of stress concentration $\alpha$ determined by the expression (19), and the expression (20) affectable with only the radius of curvature irrespective of any leg length, shape, thickness, etc. of the weld is practically usable by determining the radius of curvaure.

FIGS. 19a to 21 explain a second embodiment of the inventive method of measuring the factor of stress concentration. According to the second embodiment, the factor of stress concentration of the toe of weld E at the flange side is measured, while the first embodiment is intended for measuring the factor of stress concentration of the toe of weld W at the web side.

FIGS. 19a and 19b explain the test piece and the apparatus for measurement of the factor of stress concentration in the weld, and FIG. 19c shows as enlarged in scale the toe of weld E at the flange side in FIG. 19a. The test piece is the same in shape, material and dimensions as in the first embodiment, except for the variety of radius of curvatures $\rho_E$ being in 4 kinds: 0.4, 1.34, 3.7 and 6.0 mm. Any toes of weld other than that E of the test piece are finished by a grinder so as to have a sufficiently large radius of curvature to prevent the toe of weld E from being affected by any stress concentration. Also, the measuring apparatus for factor of stress concentration and the method of measurement are identical to those in the first embodiment, provided that the probe 3 is placed at the flange side for the ultrasound wave 4 to be emitted from the probe for incidence toward the toe of weld E at the flange side.

The relation of the echo height h with the change of mean stress $\sigma_{nw}$ was measured and the result is shown in FIG. 20. The parameter is the radius of curvature $\rho_E$ of the toe of weld E at the flange side. As seen from FIG. 20, the smaller the radius of curvature $\rho_E$, the greater the change in echo height h as the mean stress $\sigma_{nw}$, which are the same as in FIG. 17 of the first embodiment; however, with the radii of curvature $\rho_E$ being 3.7 and 6.0 mm, the echo height h shows only a little change in the range of mean stress $\sigma_{nw}$ being a maximum of 15 kg/mm². This means that the factor of stress concentration $\alpha$ is small. The relation between the radius of curvature $\rho_w$ and the factor of stress concentration $\alpha$ determined from the expression (19) is shown with small circles in FIG. 21. The regression line formed by connecting the spots plotted with the small circles to each other and indicative of the relation between the factor of stress concentration $\alpha$ and radius of curvature $\rho_E$ can be expressed as follows:

$$\alpha = 1 + \frac{1}{2\sqrt{\rho_E}} \quad (21)$$

It is seen from this expression that the factor of stress concentration $\alpha$ can be approximated from only the relation with the radius of curvature $\rho_E$. Plotting in FIG. 21 with dot line of the factors of stress concentration $\alpha$ determined by the expression (21) is relatively well coincident with the small circles indicative of the factors of stress concentration $\alpha$ determined by the expression (19). With the radius of curvature $\rho_E$ increased up to some 7.0 mm, the factor of stress concentration $\alpha$ becomes less than 1.2. On the contrary, with a small radius of curvature $\rho_E$ being as small as 0.4 mm, the factor of stress concentration $\alpha$ becomes 1.79. This value is small as compared with the values of 1.38 and 2.58 as shown in FIG. 18 of the first embodiment. It means that even with a slight difference in measuring position between the toe of weld W at the web side and that E at the flange side while the measurement is being done under same conditions, a difference in value of the factor of stress concentration can be definitely measured, which proves one aspect of the present invention that the measurement of the factor of stress concentration can be done with a high accuracy.

A third embodiment of the inventive method of the factor of stress concentration will be explained with reference to FIGS. 22a to 24. According to this third embodiment, an undercut $W_u$ is developed in the toe of weld, in place of the toe of weld W at the web side in the first embodiment, during a normal welding, and the factor of stress concentration at the bottom of the undercut $W_u$ is measured.

Figure 22A:
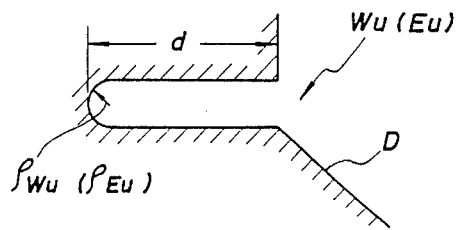
FIGS. 22a to 24 show a third example application of the present invention, FIG. 22a showing the shape of an undercut developed in the toe of weld of a test piece, FIG. 22b showing an example shape of the undercut as enlarged in scale, FIG. 23 showing the result of measurement of the relation between the mean stress and echo height taking as parameter the ratio between the radius of curvature and depth of the undercut bottom, and FIG. 24 being a graph indicative of the relation between the ratio between the radius of curvature and depth and the factor of stress concentration, determined from the measurement result in FIG. 23, in which the relation calculated from the experimental expression in an experiment of photo-elasticity is indicated with a dot line.
Figure 22B:
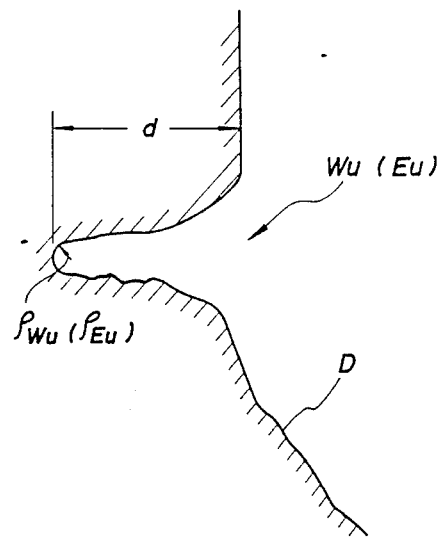

The test piece, measuring apparatus for the factor of stress concentration and method of measuring according to this third embodiment are identical to those in the first embodiment, except that the toe of weld W in FIG. 16a, having been described concerning the first embodiment, is replaced with the undercut shown in FIG. 22a. The radius of curvature $\rho_{wu}$ of the undercut bottom and the shape of the undercut of a bottom d from the plate surface to the bottom are shown by way of example in FIG. 22b. This FIG. 22b shows as enlarged in scale by 50 times the example radius of curvature $\rho_{wu}$ of 0.07 mm and depth d of 0.63 mm. The reference symbol D denotes a weld beam surface of which the toe of weld other than the undercut is finished sufficiently to prevent the toe of weld $w_u$ from being affected by any stress concentration. $\rho_{wu}/d$ in this embodiment is 0.11. The radius of curvature $\rho_{wu}$ and the depth d were measured by modeling the undercut by a replica, cutting the model into slices, and magnifying the slice by a light projector for measurement. FIG. 22a is a schematic drawing of FIG. 22b. While in the first and second embodiments, several kinds of radius of curvature of the toe of weld were measured, the ratio between the radius of curvature $\rho_{wu}$ and depth of d of the undercut bottom, namely, $\rho_{wu}/d$, is measured and the factors of stress concentration are measured of test pieces of three kinds of that ratio: 0.11, 0.14 and 0.67.

Figure 23:
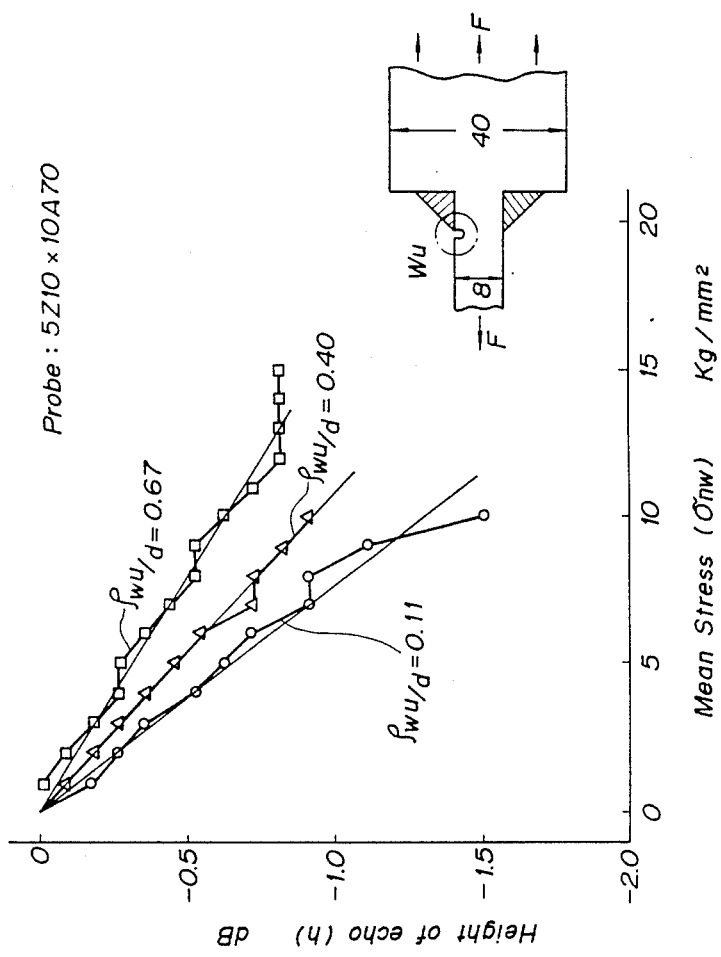

The results of measurement of the relation of the echo height h with the change of mean stress $\rho_{nw}$ are shown in FIG. 23. The parameter is $\rho_{wu}/d$. As apparent from FIG. 23, the smaller the value of the ratio $\rho_{wu}/d$, namely, the smaller and sharper the radius of curvature $\rho_{wu}$ of the undercut bottom and the larger the depth d, the steeper the gradient of the echo height h. By substituting this relation in the expression (19), the factor of stress concentration $\alpha$ at the undercut $W_u$ developed in the toe of weld at the web side can be easily determined.

Figure 24:
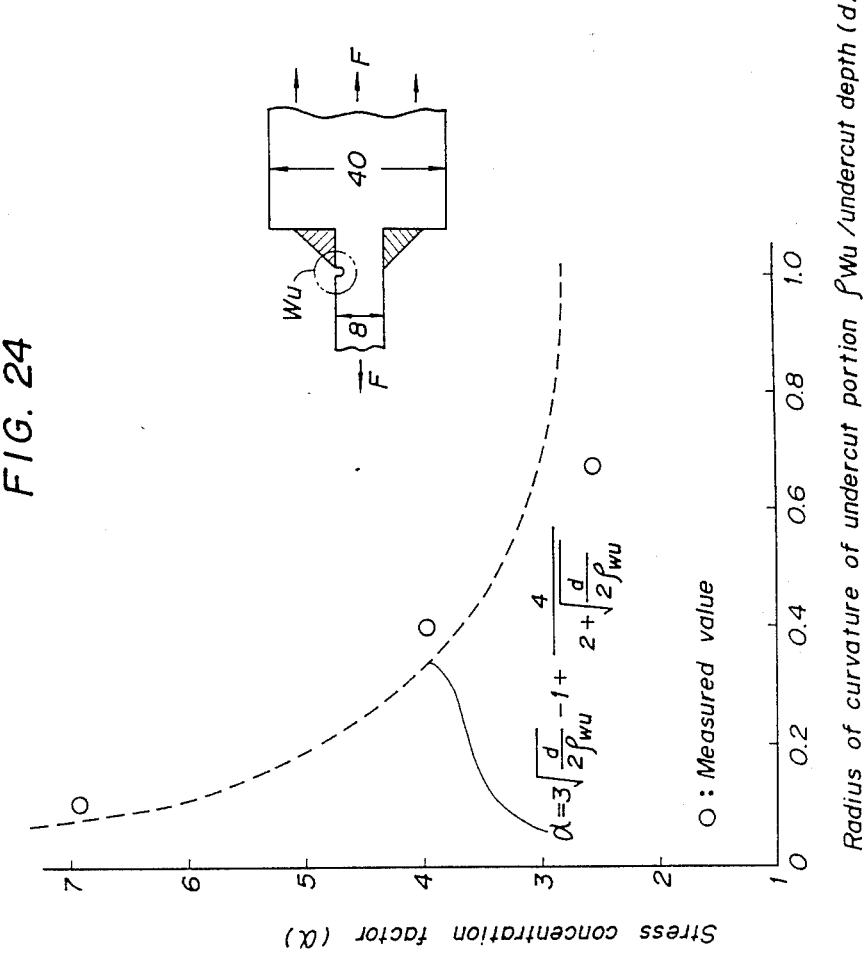

FIG. 24 shows the relation between the factor of stress concentration $\alpha$ determined by the expression (19) and the ratios $\rho_{wu}/d$ of said three kinds of test piece. The points of the factors of stress concentration are indicated with small circles in this FIG. 24. Concerning a test piece with a U-shaped nocth, the factor of stress concentration when a tensile load works in the direction in which the opening of the notch is opened had been measured in the past in a variety of photo-elasticity experiments, and experimental expressions obtained by the experiments had been proposed. For example, H. Neuber reported a following expression in 1958:

$$\alpha = 3\sqrt{\frac{d}{2\rho}} - 1 + \frac{4}{2 + \sqrt{\frac{d}{2\rho}}} \quad (22)$$

E. Inglis reported an expression as follows in 1913:

$$\alpha = 1 + 2\sqrt{\frac{d}{\rho}} \quad (23)$$

Also E. Armbruster reported the following expression in 1931:

$$\alpha = \frac{2\frac{d}{\rho} + 4\sqrt{\frac{d}{\rho}} + 2}{2 + \sqrt{\frac{d}{\rho}}} \quad (24)$$

Plotting with a dot line in FIG. 24 of the relation between the factor of stress concentration $\alpha$ determined by the expression (22) among those (22) to (24) and the ratio $\rho/d$ is relatively well coincident with the small circles indicative of the relation between the factor of stress concentration $\alpha$ determined by the expression (19) and the ratio $\rho_{wu}/d$ of the three kinds of test piece, especially at the side where the value of the factor of stress concentration $\alpha$ is large. The expression (22) also proves that with the inventive method, the factor of of stress concentration at the bottom of any undercut developed during a welding can be determined as hardly influenced by the bead shape, leg length, thickness, etc. of the weld zone, if the value of $\rho_{wu}/d$ can be measured, with such a high accuracy that the inventive method can be satisfactorily used in practice.

A fourth embodiment of the inventive method will be explained with reference to FIGS. 25 and 26. While the third embodiment is intended for measurement of the factor of stress concentration at the bottom of an undercut $W_u$ developed in the toe of weld at the web side, the fourth embodiment is to measure the factor of stress concentration at the bottom of an undercut $E_u$ developed in the toe of weld at the flange side.

The test piece, measuring apparatus for the factor of stress concentration, method of measuring, etc. in the fourth embodiment are identical to those in the second embodiment, except that the toe of weld E in FIG. 19a, having been described concerning the second embodiment, is replaced with the undercut shown in FIG. 22a. In this embodiment, the relations between the radius of curvature $\rho_{Eu}$ of the undercut bottom and the depth d from the plate surface to the undercut bottom, namely, $\rho_{Eu}/d$, are in thress kinds: 0.04, 0.32 and 0.80. The radius of curvature $\rho_{Eu}$ and the bottom d of the test piece were measured in the same manner as in the third embodiment.

Figure 25:
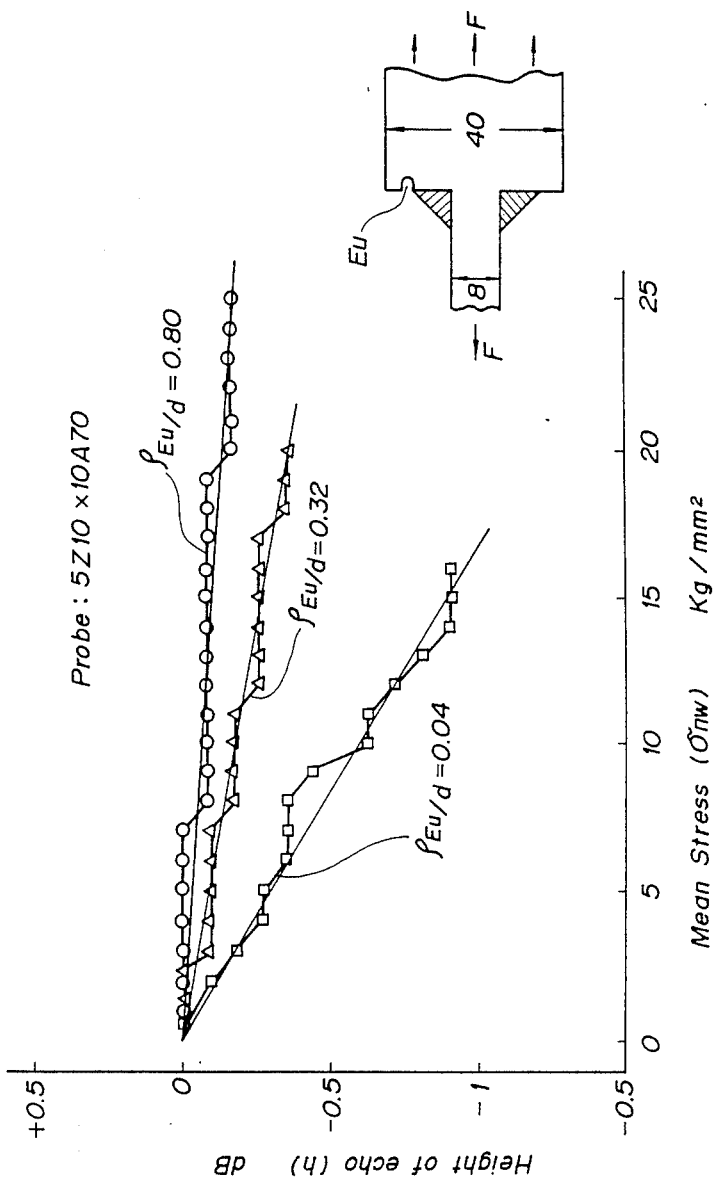
FIGS. 25 and 26 explain a fourth example application of the present invention, FIG. 25 showing the measurement result of the relation between the mean stress and echo height taking as parameter the ratio between the radius of curvature and depth of the bottom of an undercut developed in the toe of weld at the flange side, and FIG. 26 being a graph indicative of the relation between the ratio between the radius of curvature and depth and the factor of stress concentration, determined from the measurement result in FIG. 25, in which the relation calculated from the experimental expression in an experiment of photo-elasticity.

The results of the measurement of the relation between the echo height h with the change of mean stress $\sigma_{nw}$ are shown in FIG. 25. The parameter is $\rho_{Eu}/d$. The decrease of the echo height h as the mean stress $\sigma_{nw}$ increases, it is apparent from FIG. 25, is very dull as compared with that in FIG. 23 of the third embodiment, and also as compared with the factor of stress concentration of an undercut developed in the toe of weld at the web side, that of the undercut in this fourth embodiment is very small. By substituting this relation in the expression (19), the factor of stress concentration $\alpha$ at the bottom of the undercut $E_u$ with respect to the mean stress $\sigma_{nw}$ can be easily determined.

Figure 26:
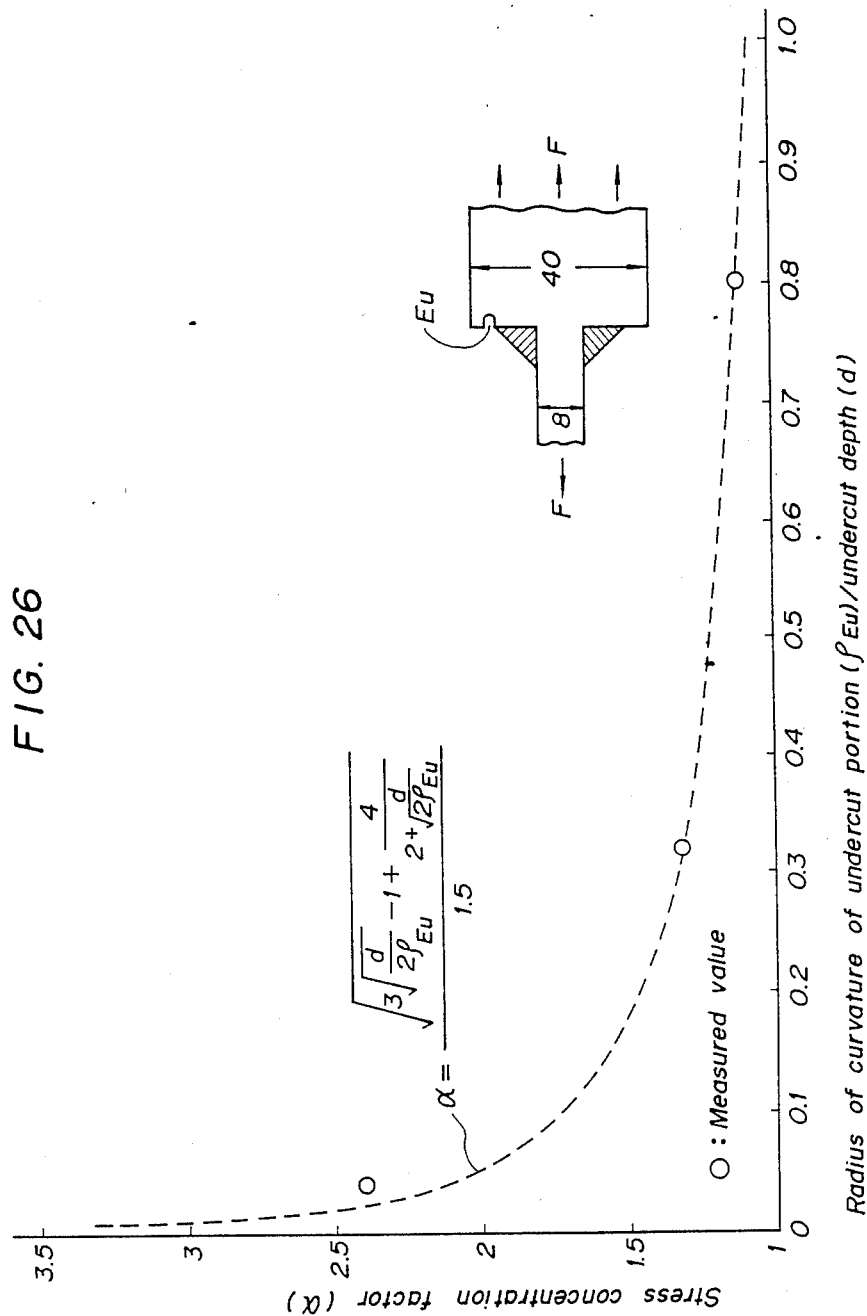

FIG. 26 shows the relation between the factor of stress concentration $\alpha$ determined by the expression (19) and the ratios $\rho_{Eu}/d$ of the three kinds of test piece, with the relations being plotted with small circles. As having been described in the description concerning the third embodiment, many photo-elasticity experiments for determing the factor of stress concentration had been done on test pieces with U-shaped notch; as the results, the expressions (22) to (24) had been reported. Plotting with dot line in FIG. 26 of the relation between the factor of stress concentration $\alpha$ determined by dividing by 1.5 the square root of the expression (22) reported by H. Neuber, namely, by the expression (25), and the ratio $\rho/d$ is nearly coincident with the small circles determined by the expression (19):

$$\alpha = \frac{\sqrt{3\sqrt{\frac{d}{2\rho}} - 1 + \frac{4}{2 + \sqrt{\frac{d}{2\rho}}}}}{1.5} \quad (25)$$

Therefore, similarly to the third embodiment, the inventive method is proved to permit to measure the factor of stress concentration at the bottom of an undercut developed in the toe of weld at the flange side without being affected by the bead shape, leg length, thickness, etc. of the weld zone but with such a high accuracy that the inventive method can be satisfactorily used in practice, if the value of $\rho_{Eu}/$ can be measured.

The method having been described in the foregoing is a visual method by which an echo is displayed on the CRT for measurement, but according to the present invention, the analogue quantity of echo height can be digitized by a well-known converting means and the correlation between the analogue quantity of the echo height and the working stress be calculated, for thereby indicating the results as numerical values. Also, such values can be stored in a memory and compared with reference values as necessary for diagnosis of the fatigue of the members of a product or machine or for preventive inspection of the latter.

It is evident to those skilled in the art that the present invention is not limited to the embodiments having been described in the foregoing, but can be varied in various forms without departing from the scope of technical concept of the present invention.

What is claimed is:

1. A method of measuring the stress concentration factor at a stress-concentrated portion of a mechanical member having an undercut located at a portion where the cross-section of the member varies abruptly, said undercut extending into the member and having a bottom, said method comprising:
   causing an ultrasonic wave to impinge on said stress-concentrated portion of said member in a first stressed state;
   detecting the acoustic pressure of the ultrasonic wave reflected from the bottom of the undercut while said member is in said first stressed state;
   gradually increasing or decreasing the stress on said member to cause an increased or decreased stressed state and in a direction for causing a variation of the shape of the bottom of the undercut;
   continuing to cause said ultrasonic wave to impinge on said stress-concentrated portion of said member;
   detecting the acoustic pressure of the ultrasonic wave reflected from said bottom of the undercut while said undercut is in the increased or decreased stressed state;
   comparing the acoustic pressure of the ultrasonic wave reflected from the bottom of the undercut in said first stressed state with the acoustic pressure when said stress concentrated portion is in the increased or decreased stressed state; and
   determining the stress concentration factor at the stress-concentrated portion using as an evaluation index the change ratio of the compared values of the acoustic pressure.

2. The method as set forth in claim 1 in which said step of increasing or decreasing the stress is effected within the limits of the elasticity of said member.

3. The method as set forth in claim 2 in which said step of increasing or decreasing the stress is effected within a range of stress in which as said stress increases, the detected acoustic pressure of the ultrasonic wave reflected from the stress-concentrated portion decreases.

4. The method as set forth in claim 1 in which said step of determining the stress concentration factor comprises using as the evaluation index the value of the correlation between the change ratio of the comparison values and the stress acting on said stress-concentrated portion.

5. The method as set forth in claim 1 in which said step of causing an ultrasonic wave to impinge on said stress-concentrated portion comprises the steps of placing a probe in close contact with a surface of the member having a stress-concentrated portion in a stressed state, and impinging said ultrasonic wave on said stress-concentrated portion with the probe kept in place at the point of close contact.

6. The method as set forth in claim 5 in which said step of placing the probe comprises placing it at a position spaced from the stress-concentrated portion, which position is not influenced by the stress in said stress-concentrated portion.

* * * * *